US006936718B2

(12) United States Patent
Chen et al.

(10) Patent No.: US 6,936,718 B2
(45) Date of Patent: Aug. 30, 2005

(54) PREPARATION OF ROTAMER MIXTURES OF PHARMACEUTICAL SALTS

(75) Inventors: Minzhang Chen, Plainsboro, NJ (US); Bosco D'sa, Edison, NJ (US); William Leong, Westfield, NJ (US); Suhan Tang, Edison, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 10/305,100

(22) Filed: Nov. 26, 2002

(65) Prior Publication Data

US 2003/0139446 A1 Jul. 24, 2003

Related U.S. Application Data

(60) Provisional application No. 60/373,778, filed on Apr. 19, 2002, and provisional application No. 60/334,330, filed on Nov. 29, 2001.

(51) Int. Cl.$^7$ .................... C07D 211/54; C07D 211/30
(52) U.S. Cl. ....................................... 546/188; 546/190
(58) Field of Search ................................. 546/188, 190

(56) References Cited

U.S. PATENT DOCUMENTS 6,329,393 B1 * 12/2001 Amato et al. ............... 514/326
6,387,930 B1 * 5/2002 Baroudy et al. ............ 514/316

FOREIGN PATENT DOCUMENTS

WO   WO 00/66559   11/2000

OTHER PUBLICATIONS

Salt Selection for basic drugs 1986, Philip Gould.*
Ananda Palani et al Discovery of 4–[(Z)–](4–Bromo . . . Oct. 11, 2001.*
Julie Strizki et al SCH– C (SCH 351125), . . . Oct. 2001.*
Rizzo et al., "Equilibrium and Kinetics of Rotamer Interconversion in Immunosuppressant Prodigiosin Derivatives in Solution", *J. Pharmaceutical Sciences*, Jan. 1999, 88(1):73–78.
Palani et al., "Discovery of 4–[(Z)–(4–Bromophenyl)–(ethoxyimino)methyl]–1'–[2, 4–dimethyl–3–pyridinyl)carbonyl]–4'–methyl–1,4'–bipiperidine N–Oxide (SCH 351125): An Orally Bioavailable Human CCR5 Antagonist for the Treatment of HIV Infection", *J. Medical Chemistry*, Oct. 11, 2001, 44(21): 3339–3342.
S. Berge et al., "Pharmaceutical Salts", *J. of Pharmaceutical Sciences*, 66(1): 1–19 (1977).
P. Gould et al., "Salts Selection for Basic Drugs", *International J. of Pharmaceuticsl*, 33:201–217 (1986).

* cited by examiner

*Primary Examiner*—Rita Desai
(74) *Attorney, Agent, or Firm*—Palaiyur S. Kalyanaraman

(57) ABSTRACT

In one embodiment, the present invention discloses a process to directly prepare an unequal ratio of specific, preferred rotamer or rotameric pair of an acid salt from a basic compound, by creative choice of a solvent medium. The process is particularly useful in preparing desired rotamers of pharmaceutically useful salts.

39 Claims, No Drawings

PREPARATION OF ROTAMER MIXTURES OF PHARMACEUTICAL SALTS

FIELD OF THE INVENTION

This patent application generally discloses a novel process to prepare pharmaceutically useful salts. It specifically discloses a novel process to synthesize pharmaceutically useful salts of 4-[(4-bromophenyl)(ethoxyimino)methyl]-1'-[(2,4-dimethyl-1-oxido-3-pyridinyl)carbonyl]-4'-methyl-1,4'-Bipiperidine, and especially pharmaceutically useful salts of 4-[(Z)-(4-bromophenyl)(ethoxyimino)methyl]-1'-[(2,4-dimethyl-1-oxido-3-pyridinyl)carbonyl]-4'-methyl-1,4'-Bipiperidine. It further discloses a process to prepare pharmaceutical salts that are enriched in desired specific rotameric configurations. This application claims priority from U.S. provisional patent application, Docket No. 60/334,330 filed Nov. 29, 2001 and U.S. provisional patent application, Docket No 60/373,778 filed Apr. 19, 2002.

BACKGROUND OF THE INVENTION

4-[(Z)-(4-bromophenyl)(ethoxyimino)methyl]-1'-[(2,4-dimethyl-1-oxido-3-pyridinyl)carbonyl]-4'-methyl-1,4'-bipiperidine (Formula I) is disclosed in pending, commonly-owned U.S. patent application Ser. No. 60/329,566, filed Oct. 15, 2001.

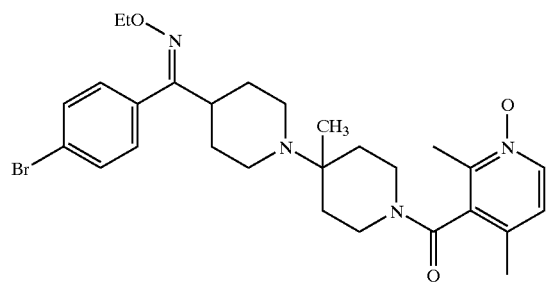

The compound of Formula I is also disclosed in the commonly owned U.S. patent application Ser. No. 09/562,815, filed May 1, 2000, the disclosure of which is incorporated herein by reference. That provisional patent application discloses several novel antagonists of the CCR5 receptor which are useful for the treatment of AIDS and related HIV infections. CCR-5 receptors have also been reported to mediate cell transfer in inflammatory diseases such as arthritis, rheumatoid arthritis, atopic dermatitis, psoriasis, asthma and allergies, and inhibitors of such receptors are expected to be useful in the treatment of such diseases, and in the treatment of other inflammatory diseases or conditions such as inflammatory bowel disease, multiple sclerosis, solid organ transplant rejection and graft v. host disease.

Generally, pharmaceutical compounds are used as their pharmaceutically acceptable salts. This is also true of CCR5 receptor antagonists such as the compound of Formula I, which makes the preparation of pharmaceutically acceptable salts of such compounds quite important.

The compound of Formula I has no chiral centers and the geometry of the oxime is controlled as the Z configuration by the chemical synthesis. However, the compound of Formula I exists as a mixture of rotational isomers or rotamers due to the restricted rotation about the two single bonds, marked a and b in FIG. 1. The relative relationship between the four rotamers is depicted in Scheme 1. As such Structures A and B have a diastereomeric relationship and Structures C and D have a diastereomeric relationship.

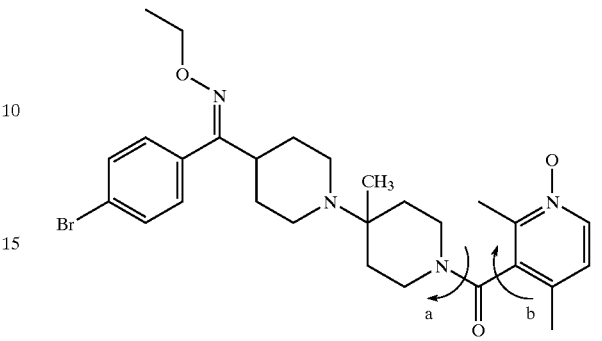

FIG. 1

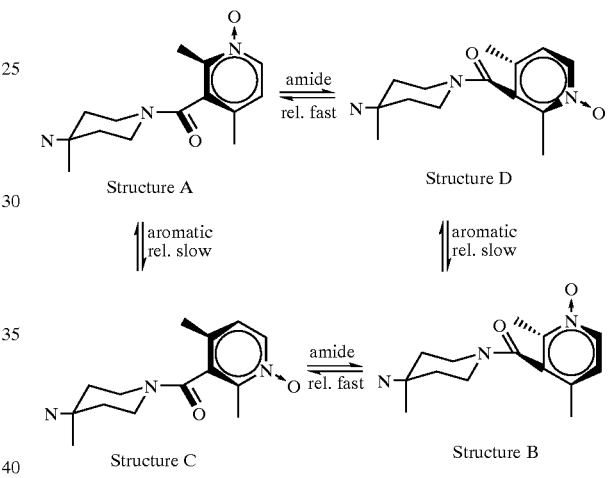

Scheme 1

For convenience, the four rotamers are denoted as isomers 1, 2, 3 and 4, in order of their elution from a chiral HPLC column.

While general synthetic approaches for salts typically yield a 1:1:1:1 ratio of the rotamers 1, 2, 3 and 4, it would be preferable to find methods of synthesis that would yield rotamer populations that are enriched in certain rotamers preferentially.

SUMMARY OF THE INVENTION

In an embodiment, the present invention discloses a process for preparing a mixture of rotamers or rotamer pairs of a salt of a basic compound wherein said mixture comprises one or more rotamers or rotamer pairs of the salt in a higher (i.e., preferentially enriched) molar percent than other corresponding rotamers or rotamer pairs of the salt, with the process comprising reacting said basic compound with an acid in admixture with a solvent. The invention also teaches a method for preparing pharmaceutically useful salts. Additionally, it teaches a method for the formation of the salts, pharmaceutically useful or otherwise, of the compound of Formula I in high yields. It also teaches the direct preparation of specific rotamers or rotamer pairs of a salt of the compound of Formula I in high yields and in higher molar percent than other corresponding rotamers or rotameric pairs of the salt. In doing so, the process maintains the stereochemistry of the oxime in the compound of Formula I undisturbed. In addition, it enables the formation of a mixture of rotamers or rotamer pairs of a salt of a basic compound wherein said mixture comprises one or more rotamers or rotamer pairs of the salt in a higher molar percent than other corresponding rotamers or rotamer pairs of the salt, with the salt being prepared by a process comprising reacting said basic compound with an acid in admixture with a solvent.

The term "high yields" refers to at least about 55% yield of the desired, preferentially enriched product. Thus, unlike previously known processes which result in a 1:1:1:1 ratio of the salts of the rotamers 1, 2, 3 and 4 which then need separation or some treatment to enrich in desired rotamer(s), the present process offers a way to obtain the selective formation of the desired rotamers or rotamer pairs in higher molar percent than other corresponding rotamers or rotameric pairs directly. The term "higher molar percent" refers to selective, preferential formation of certain preferred rotamers (or rotamer pairs) over other rotamers (or rotamer pairs) by about in a 45:55 molar percent ratio. The term 'directly' means 'without the need for an additional step to separate the 50:50 rotamers or rotamer pairs obtained', for example, as in the conventional process. Thus, for example, in one instance, the present process yields ratios of 2.5:2.5:47.5:47.5 mole percent of salts of the rotamers 1:2:3:4 respectively, as determined by NMR and HPLC. The above-noted ratio 2.5:2.5:47.5:47.5 is more conveniently termed 5:95 peaks A:B to denote the appearance of (the 1,2 rotamers versus the 3,4 rotamers) when observed under achiral chromatographic conditions. Stated another way, the present process offers a way to directly obtain, for example, even 95 mole percent of the 3,4 isomers in the salt. Thus, for example, if the 3,4 isomer pair is the desired one with high pharmaceutical activity, the present process makes it possible to obtain that isomer pair directly instead of having to make an equimolar mixture of the 1,2 isomer pair and 3,4 isomer pair by previously known processes, followed by cumbersome separation of the mixture; such a separation may or may not yield the desired salt in decent yields and the process is also likely to be expensive. Additionally, in the case of certain salts, the present unique process offers the selective formation of the salt of only one enantiomer. Since the activity of pharmaceutical compositions may differ depending upon the type of salt they are comprised of, the present process affords a unique way to obtain desired specific salts with good pharmaceutical activity in highly enriched enantiomeric content. In the case of the compound of Formula I, the present process achieves such preferential formation of the isomers by creative selection of the acid (for salt formation) and solvent medium for the reaction. In the case of the pharmaceutically useful salts of the compound of Formula I, the 3,4-isomer pair is preferred over the 1,2-isomer pair for pharmaceutical activity.

The inventive process to make different rotamers of the salts of the compound of Formula I has several advantages: it is economical, can be easily scaled-up and yields the desired ratio in high yields.

DESCRIPTION OF THE INVENTION

In one embodiment, the present invention discloses a novel, easy-to-use process for preparing a pharmaceutical salt of the compound of Formula I in high yields. It also teaches the preferential preparation of specific rotamers or rotamer pairs of the salt of the compound of Formula I in high yields. The present process comprises reacting the compound of Formula I (or a similar base) with an acid in admixture with a selected solvent medium in order to obtain differing ratios of rotamers as salts. The term "admixture" refers to physical contact of the ingredients as is known to those skilled in the art such as, for example, solution, suspension, emulsion, contact through a matrix such as, running through a column, and the like. In an illustration, as shown in one of the following EXAMPLES, the diastereoisomeric ratio of the 1,2 pair to the 3,4 pair in the solid benzene sulfonate salt of the compound of Formula I is respectively 4:96 when prepared in acetone. However, that ratio changes to 7:93 when prepared in MTBE, to 80:20 when prepared in THF, to 95:5 when prepared in toluene or acetonitrile or water. Other salts may be prepared similarly by changing the acid and the solvent as shown later.

The process, while described and illustrated herein as the preparation of specific desired rotamers of the compound of Formula I, is simple enough to be applicable generically to the preparation of pharmaceutically useful salts from basic pharmaceutical compositions. By appropriate choice of the solvent medium, the reaction of the basic compound with an acid (from which the salt is to be derived) to form the salt selectively yields the desired rotameric compositions in enriched molar percent. Thus, in another embodiment, the invention offers a novel, simple process to directly prepare desired salts of basic compounds in unequal ratio of rotamers or rotameric pairs. In yet another embodiment, the present invention teaches the formation of pharmaceutically useful salts in high yields and selectivity of rotamer population.

The following non-limiting list includes anions representing suitable acids which may be used to form salts in accordance with the present invention. The list of anions for useful salts includes, for example, acetate, benzene sulfonate, benzoate, bicarbonate, bromide, calcium edetate, camphorsulfonate, carbonate, chloride/dihydrochloride, citrate, N,N-di(dehydroabietyl)ethylenediamine, edetate, 1,2-ethanedisulfonate, ethanesulfonate, fumarate, glucoheptonate, gluconate, glutamate, p-glycollamidophenylarsonate, hexylresorcinate, hyclate, hydrobromide, hydrochloride, 2-hydroxyethanesulfonate, hydroxynaphthoate, iodide, lactate, lactobionate, lauryl sulfonate, malate, maleate, mandelate, methanesulfonate, methylbromide, methylnitrate, methylsulfate, mucate, nafate, napsylate, nitrate, pamoate, pantothenate, phosphate/diphosphate, polygalacturonate, salicyclate, sodium succinate, stearate, subacetate, succinate, sulfate, tosylate, tannate, tartrate/bitartarte, 8-chlorotheophyllinate, triethiodide, adipate, alginate, aminosalicyclate, anhydromethylenecitrate, arecoline, asparate, bisulfate, butylbromide, camphorate, digluconate, dihydrobromide, disuccinate, glycerophosphate, hemisulfate, hydrofluoride, hydroiodide, methylenebis(salicyclate), naphthalenedisulfonate, oxalate, pectinate, persulfate, phenylethylbarbiturate, picrate, propionate, thiocyanate, undecanoate, acetylaminoacetate, N-acetyl-L-asparaginate, N-acetylcystinate, adamantoate, adipoate, N-alkylsulfamates, anthraquinone-1,5-disulfonate, arabolactansulfate, argininate, aspartate, betaine, carnitine, 4-chloro-m-toluenesulfonate, decanoate, diacetyl sulfate, dibenzylethylenediamine, dimethylamine, diguaiacylphosphate, dioctylsulfosuccinate, pamoate, fructose-1,6-diphosphate, glucose phosphate, L-glutaminate, hydroxynaphthoate, lauryl sulfate, lysine, 2-naphthenesulfonate, octanonate, tannate and theobromine acetate. Additionally, acids which are generally considered suitable for the formation of pharmaceutically useful salts from basic pharmaceutical compounds are discussed, for example, by S. Berge et al, *Journal of Pharmaceutical Sciences* (1977) 66(1),1–19; P. Gould, *International J. of Pharmaceutics* (1986) 33 201–217; Anderson et al, *"The Practice of Medicinal Chemistry"* (1996), Academic Press, New York; Stahl, et al, *"Handbook of Pharmaceutical Salts: Properties, Selection and Use"* (2002), Wiley-VCH, Zurich; and in *The Orange Book* (Food & Drug Administration, Washington, D.C. on their website). These disclosures are incorporated herein by reference.

Generally, known processes to form salts by reaction of basic compounds with acids yield equal ratios of rotamers or rotameric pairs which need to be later separated in yet another step. The present process, which avoids such separation by preferentially enriching in certain rotamer populations during the salt formation reaction itself is superior.

The present process may be illustrated by the formation of the benzene sulfonate salt of the compound of Formula I. The compound of Formula I, which is basic, may be dissolved or otherwise intimately mixed or suspended in a suitable solvent medium. Suitable solvent media are, for example, ketone, ether, hydrocarbon or mixtures thereof. Suitable ketones include, for example, acetone, methyl ethyl ketone, methyl n-amyl ketone and the like and mixtures thereof, preferably acetone. Suitable ethers are, for example, tetrahydrofuran, diglyme, methyl ethyl ether and mixtures thereof, preferably tetrahydrofuran. Suitable hydrocarbons are, for example toluene, xylene, chlorobenzene, hexane, heptane and mixtures thereof, preferably toluene. Benzene sulfonic acid may be added to this either as solid or as a solution (or intimate mixture or suspension) in the same solvent. The acid is used generally in 0.9:1.1 mole ratio, preferably in a 0.9:1 molar ratio and typically in 1:1 molar ratio, with respect to the compound of Formula I. The total quantity of the solvent may be about a 20:1 ratio, preferably about a 18:1 ratio and typically about a 15:1 ratio, with respect to the compound of Formula I. The mixture is stirred or mixed otherwise, generally at about 25–70° C., preferably at about 25–60° C. and typically at about 40–60° C. for about 1–15 hours, and then kept at about the ambient conditions to allow the completion of crystal formation of the salt. The salt may be isolated by filtration or such similar methods. When acetone was used as the ketone solvent in an Example, a diastereomeric ratio of 4:96 (for the 1,2 isomer pair to the 3,4 isomer pair) was found in the benzene sulfonate salt so formed.

If the compound of Formula I Is dissolved in an ether solvent such as tetrahydrofuran and treated with benzene sulfonic acid as a solid or as dissolved (or mixed or suspended) in tetrahydrofuran in the process noted above, a diatereoisomeric ratio of 5:95 of the above-noted isomer pairs Is obtained. If, instead of the ether alone, the solvent is changed to a mixture of an ether and a hydrocarbon, the diastereomeric ratio in the thus-obtained salt changes to 40:60.

Yet another example is the preparation of the tosylate salt (or p-toluene sulfonate) of the compound of Formula I. If the tosylate salt is prepared from the compound of Formula I and p-toluene sulfonic acid in an ether solvent for example, a diastereomeric ratio of 99:1 is obtained for the 1,2 isomer pair to the 3,4 isomer pair. If, however, the solvent is changed to a ketone for example, the same ratio changes to 7:93 in the salt obtained.

It is also possible to obtain only one enantiomer form of the salt instead of a pair. Thus, for example, the reaction of the compound of Formula I with dibenzoyl tartaric acid in a ketone solvent such as, for example, acetone, methyl ethyl ketone, methyl n-amyl ketone or mixtures thereof, preferably acetone, yields a single enantiomer (rotamer 1) in more than 95% yield. Depending upon whether the starting acid was the D- or L-form of the acid, the single enantiomer form of the salt has the same D- or L-configuration.

The salts prepared by the present invention exhibit desirable physical and chemical characteristics suitable for pharmaceutical uses. Non-limiting examples of such characteristics include physical stability, chemical stability, thermal stability, desirable hygroscopicity, solubility, fluidity and the like.

The following nonlimiting EXAMPLES and TABLE 1 are provided in order to further illustrate the present invention.

EXAMPLES

Unless otherwise stated, the following abbreviations have the stated meanings in the Examples and Table 1 below:
HPLC=High Performance Liquid Chromatography
M.pt: melting point
NMR=nuclear magnetic resonance spectroscopy
mL=milliliters
g=grams
rt=room temperature (ambient)
DMSO=dimethylsulfoxide
THF=Tetrahydrofuran
MTBE=Methyl t-butyl ether
ACN=Acetonitrile
EtOH=Ethanol
MeOH=Methanol
IPA=Isopropyl alcohol
EtOAc=Ethyl acetate
iPrOH=Isopropyl alcohol
iPrOAc=Isopropyl acetate
TMSI=Trimethylsilyl iodide

EXAMPLES

Example 1

Preparation of the Benzene Sulfonic Acid Salt of the Compound of Formula I (4:96)

The amine compound of Formula I (70 g, 125.6 mmol) was taken up in acetone (700 mL). To this solution was added, benzene sulfonic acid (19.9 g, 125.8 mmol) dissolved in acetone (350 mL). The reaction mixture was agitated at 45–60° C. for 12 hours, and then cooled to 20–25° C. over 4 hours. After 3 hours, the heterogeneous reaction mixture was filtered and the solids were washed twice with acetone (140 mL). The isolated yield was 80–88%. The solids were 96% of (3+4) rotamers by HPLC. $^1$H NMR (400 MHz, D$_2$O, mixture of diastereomers) δ 8.2 (d, J=6.6 Hz, 1H), 7.7 (d, J=7.3 Hz, 2H), 7.6 (d, J=6.7 Hz, 2H), 7.5 (m, overlapping, 3H), 7.4 (d, J=6.6 Hz, 1H), 7.2 (d, J=7.3 Hz, 2H), 4.6 (br, unresolved m, 1H), 4.0 (q, J=7.0 Hz, 2H), 3.7 to 3.5 (br, overlapping unresolved, m, 3H), 3.3 (t, J=6.6 Hz, 1H), 3.1 (br, overlapping, 3H), 2.9 (m, 1H), 2.4 (s, 3H), 2.3 (s, 3H), 2.2 to 1.9 (br, overlapping m, 4H), 1.8 (br, unresolved, m, 4H), 1.4 (s, 3H), 1.1 (t, J=7.0 Hz, 3H); $^{13}$C NMR (400 MHz, D$_2$O, mixture of diastereomers) δ 166.8, 146.2, 143.2, 140.8, 139.9, 134.2, 132.6, 132.3, 130.2, 129.8, 127.3, 126.2, 123.7, 70.6, 65.2, 46.6, 43.5, 40.1, 38.9, 34.1, 33.2, 27.7, 18.8, 15.7, 15.0, 14.7, 14.5; M.P. 195.5° C.

HRMS calcd for $C_{28}H_{37}BrN_4O_3$ 557.2127. found 557.2126.

Example 2

Citric Acid Salt of the Compound of Formula I (93:7)

To a solution of 2.0 g of the compound of Formula I in 30 mL of EtOH at room temperature, 0.7 g of citric acid is added. After stirring at room temperature for 3 days, the corresponding salt is isolated by filtration as a white solid with a 93:7 rotamer ratio.

Example 3

Preparation of the Fumarate Salt of the Compound of Formula I (95:5)

The amine compound of Formula I (21.0 g, 37.7 mmol) was dissolved in denatured ethyl alcohol (105 mL). The resulting solution was heated to 60° C. To this was added a solution of fumaric acid (4.8 g, 41.3 mmol) in denatured ethyl alcohol (105 mL). The reaction mixture was stirred at 60–65° C. for 12 hours, and was then cooled to 20–25° C. The heterogeneous reaction mixture was filtered and the solids were washed with denatured ethyl alcohol (21 mL). The isolated yield was 75–85%. The solids were 95% of (1+2) rotamers. $^1$H NMR (400 MHz, CD$_3$OD, mixture of diastereomers) δ 8.3 (d, J=6.7 Hz, 1H), 7.6 (d, J=8.4 Hz, 2H), 7.3 (d, J=6.7 Hz, 1H), 7.2 (d, J=8.4 Hz, 2H), 6.6 (s, 2H), 4.7 (br, unresolved m, 1H), 4.0 (q, J=7.0 Hz, 2H), 3.7 and 3.2 (br, overlapping unresolved, m, 3H), 3.3 (br, 1H), 3.1 (br, overlapping, 3H), 2.9 (m, 1H), 2.4 (s, 3H), 2.2 (s, 3H), 2.1 (br, unresolved m, 3H), 1.9 and 1.8 (br, overlapping, m, 5H), 1.5 (s, 3H), 1.1 (t, J=7.0 Hz, 3H); $^{13}$C NMR (400 MHz, CD$_3$OD, mixture of diastereomers): δ 1 70.5, 165.4, 158.0, 145.8, 140.3, 138.4, 136.2, 134.6, 132.5, 130.8, 129.2, 127.3, 125.6, 122.9, 69.8, 64.7, 46.0, 42.9, 41.5, 30.0, 33.8, 32.9, 27.7, 26.3, 18.4, 17.1, 15.7, 15.0, 14.7, 14.4, 13.8, 13.5. M.P. 228.2° C.

| Fumarate salts from alternative solvents (0.9–0.94 eq. of fumaric acid used) | |
|---|---|
| 1 MeOH/reflux 19 hr/cooled to 10° C. | (1,2):(3,4) = 97:3; 0.4% E-isomer |
| 2. EtOH/70–75° C. 19 hr/cooled to 10° C. | (1,2):(3,4) = 96.5:3.5; 0.3% E-isomer |
| 3. EtOH/60–65° C. 19 hr/cooled to 10° C. | (1,2):(3,4) = 96.5:3.5; 0.01% E-isomer 83% isolated yield. |
| 4. i-PrOH/80° C. 19 hr/cooled to 10° C. | (1,2):(3,4) = 90:10 |
| 5. MeCN/80° C. 19 hr/cooled to 10° C. | (1,2):(3,4) = 94:6 |
| 6. Acetone/reflux 19 hr/cooled to 10° C. | (1,2):(3,4) = 92.5:7.5 |
| 7. MeOH:i-PrOH (3:1)/reflux 2 hr/RT, 14 hr | (1,2):(3,4) = 97.4:2.6 80% isolated yield. |
| 8. EtOH/l-PrOH (4:1)/reflux 2 hr/RT, 14 hr | (1,2):(3,4) = 95:5 83% isolated yield. |
| 9. EtOH/reflux, 21 hr/10° C. 1 hr. | (1,2):(3,4) = 96:4 83% isolated yield. |
| 10. EtOH/reflux 6 hr/5° C. 1 hr. | (1,2):(3,4) = 95.2:4.8. |

Example 4

Hydrochloride Salt of the Compound of Formula I (95:5)

The amine compound of Formula I (0.5 g, 0.9 mmol) was taken up in isopropyl alcohol (5 mL). HCl in isopropyl alcohol (0.9 mL, 0.9 mmol) was added. The resulting suspension was stirred 80° C. for 12 hours and then cooled to 0° C. over 3 hours. The solids were filtered and washed twice with ice-cold isopropyl alcohol (5 mL). The solids were >94% of (1+2) rotamers. The isolated yield was 80–90%. $^1$H NMR (400 MHz, D$_2$O, mixture of diastereomers) δ 8.2 (d, J=6.8 Hz, 1H), 7.6 (d, J=8.4 Hz, 2H), 7.4 (d, J=6.7 Hz, 1H), 7.2 (d, J=8.4 Hz, 2H), 4.7 (br, unresolved m, 1H), 4.0 (q, J=7.0 Hz, 2H), 3.7 and 3.5 (br, overlapping unresolved, m, 3H), 3.3 (br, 1H), 3.1 (br, overlapping, 3H), 2.9 (m, 1H), 2.4 (s, 3H), 2.2 (s, 3H), 2.1 (br, unresolved m, 3H), 2.0 (br, unresolved, m, 1H), 1.8 (br, unresolved, m, 4H), 1.4 (s, 3H), 1.1 (t, J=7.0 Hz, 3H); $^{13}$C NMR (400 MHz, D$_2$O, mixture of diastereomers) δ 166.8, 161.8, 159.4, 146.2, 140.9, 139.9, 134.2, 132.6, 132.5, 132.2, 130.2, 130.1, 127.2, 123.7, 70.7, 70.6, 65.3, 46.6, 43.6, 43.4, 40.1, 38.9, 35.1, 34.1, 33.2, 27.7, 25.3, 18.4, 15.7, 14.8, 14.6, 14.4. M.P. 208.1° C. HRMS calcd for C$_{28}$H$_{37}$BrN$_4$O$_3$ 557.2127. found 557.2131.

Example 5

Hydrochloride Salt (5:95)

To an agitated solution of the compound of Formula I (1.0 g) in 10 mL of acetone was added 0.45 mL of hydrochloride solution (4.0N in isopropanol). After overnight agitation, the mixture was filtered to afford white solids with a 5:95 rotamer ratio.

Example 6

3-Hydroxy-2-naphthoic Acid Salt (12:88)

To an agitated solution of the compound of Formula I (1.0 g) in 10 mL of acetone was added a solution of 0.34 g of 3-hydroxy-2-naphthoic acid in 3 mL of EtOH. After overnight agitation, the mixture was filtered to afford white solids with a 12:88 rotamer ratio.

Example 7

L-Malic Acid Salt of the Compound of Formula I (93:7)

To a solution of 2.4 g of the compound of Formula I in 25 mL of acetone at room temperature, 0.5 g of L-malic acid is added. After stirring at room temperature overnight, the corresponding salt is isolated by filtration as a white solid with a 93:7 rotamer ratio.

Example 8

L-Malic Acid Salt of the Compound of Formula I (8:92)

To a solution of 19 g of the compound of Formula I in 40 mL of acetone at room temperature, 4.3 g of L-malic acid in 20 mL EtOH is added. After stirring at 0° C. overnight, the corresponding salt is isolated by filtration as a white solid with a 8:92 rotamer ratio.

Example 9

(S)-Mandelic Acid Salt of the Compound of Formula I (93:7)

To a solution of 3.0 g of the compound of Formula I in 16 mL of acetonitrile at room temperature, 0.8 g of (S)-mandelic acid is added. After stirring at room temperature overnight, the corresponding salt is isolated by filtration as a white solid with a 93:7 rotamer ratio.

Example 10

Mucic Acid Salt of the Compound of Formula I (52:48)

To a solution of 3.0 g of the compound of Formula I in 40 mL of methanol at room temperature, 1.1 g of mucic acid is added. After stirring at room temperature overnight, the corresponding salt is isolated by filtration as a white solid with a 52:48 rotamer ratio.

Example 11

Salicylic Acid Salt (95:5)

To an agitated solution of the compound of Formula I (1.0 g) in 10 mL of isopropyl acetate was added a solution of 0.25 g of salicylic acid in 1 mL of EtOH. After overnight agitation, the mixture was filtered to afford white solids with a 95:5 rotamer ratio.

Example 12

Succinic Acid Salt of the Compound of Formula I (83:17)

To a solution of 3 g of the compound of Formula I in 6 mL MeOH at room temperature, 0.63 g of succinic acid is added. After stirring at room temperature overnight, the corresponding salt is isolated by filtration as a white solid with a 83:17 rotamer ratio.

Example 13

P-Toluene Sulfonic Acid Salt (7:93)

To an agitated solution of 5 g of the compound of Formula I free base in 100 mL of acetone was added 1.7 g of p-toluene sulfonic acid. After overnight agitation, the mixture was filtered to afford white solids with a 7:93 rotamer ratio.

Example 14

P-Toluene Sulfonic Acid Salt (97:3)

To an agitated solution of 5 g of the compound of Formula I free base in 25 mL of acetonitrile was added 1.7 g of p-toluene sulfonic acid. After overnight agitation, the mixture was filtered to afford white solids with a 97:3 rotamer ratio.

Example 15

P-Toluenesulfonic Acid in THF (99:1)

To a solution of 5.0 g (9.0 mmol) of 351125-S in 25 mL of THF was added 1.7 g (8.9 mmol) of p-toluene sulfonic acid. The resulting mixture was heated to reflux overnight, cooled to room temperature, and filtered to give a solid with a rotamer ratio of 99:1.

Example 16

Trans-Aconitic Acid Salt of the Compound of Formula I (91:9)

To a solution of 3.0 g of the compound of Formula I in 6 mL of EtOH at room temperature, 0.9 g of trans-aconitic acid is added. After stirring at room temperature overnight, the corresponding salt is isolated by filtration as a white solid with a 91:9 rotamer ratio.

Example 17

Cis-Aconitic Acid Salt of the Compound of Formula I (58:42)

To a solution of 3.0 g of the compound of Formula I in 6 mL of EtOH at room temperature, 0.9 g of cis-aconitic acid is added. After stirring at room temperature overnight, the corresponding salt is isolated by filtration as a white solid with a 58:42 rotamer ratio.

Example 18

D-Camphoric Acid Salt of the Compound of Formula I (5:95)

To a solution of the compound of Formula I (100 g, 179 mmol) in ethyl alcohol (800 mL) was added D-camphoric acid (34.1 g, 171 mmol) dissolved in ethyl alcohol (70 mL). The reaction mixture was stirred at 56° C. for 3 hours and then cooled to 0° C. The solids were filtered and washed with ethyl alcohol (200 mL). The isolated yield was 65–85%. The solids were >95% of (3+4) rotamers by HPLC. $^1$H NMR (400 MHz, $D_2O$, mixture of diastereomers) δ 8.2 (d, J=6.6 Hz, 1H), 7.6 (d, J=7.3 Hz, 2H), 7.4 (d, J=6.7 Hz, 1H), 7.2 (d, J=6.6 Hz, 2H), 4.7 (br, unresolved m, 1H), 4.0 (q, J=7.0 Hz, 2H), 3.7 to 3.5 (br, overlapping unresolved, m, 3H), 3.3 (t, J=6.6 Hz, 2H), 3.1 (br, overlapping, 3H), 2.9 (m, 1H), 2.7 (t, J=6.6 Hz, 2H), 2.4 (s, 3H), 2.3 (s, 3H), 2.2 and 2.1 (br, overlapping m, 4H), 1.7 to 1.9 (br, unresolved, m, 6H), 1.4 (s, 3H), 1.2 (s, 3H), 1.1 (m, overlapping, 6H), 0.8 (s, 3H);

$^{13}$C NMR (400 MHz, $D_2O$, mixture of diastereomers) δ 166.9, 146.2, 140.7, 139.9, 134.2, 132.6, 132.1, 130.1, 127.3, 70.6, 65.3, 57.6, 55.3, 46.7, 43.5, 40.1, 34.0, 33.7, 33.1, 27.7, 23.8, 23.5, 22.0, 21.9, 18.8, 15.0, 14.7, 14.4. HRMS calcd for $C_{28}H_{37}BrN_4O_3$ 557.2127. found 557.2131. M.P. 195.6° C.

Example 19

1,2-Cis-cyclohexanedicarboxylic Acid Salt of the Compound of Formula I (78:12)

To a solution of 3.0 g of the compound of Formula I in 8 mL of THF at room temperature, 0.93 g of 1,2-cis-cyclohexanedicarboxylic acid is added. After stirring at room temperature overnight, the corresponding salt is isolated by filtration as a white solid with a 78:22 rotamer ratio.

Example 20

1,2-trans-cyclohexanedicarboxylic Acid Salt of the Compound of Formula I (83:17)

To a solution of 3.0 g of the compound of Formula I in 10 mL of THF at room temperature, 0.93 g of 1,2-trans-cyclohexanedicarboxylic acid is added. After stirring at room temperature overnight, the corresponding salt is isolated by filtration as a white solid with a 83:17 rotamer ratio.

Example 21

(R)-Citramalic Acid Salt of the Compound of Formula I (77:23)

To a solution of 3.0 g of the compound of Formula I in 10 mL of methanol at room temperature, 0.80 g of (R)-citramalic acid is added. After stirring at room temperature overnight, the corresponding salt is isolated by filtration as a white solid with a 77:23 rotamer ratio.

Example 22

Citraconic Acid Salt of the Compound of Formula I (86:14)

To a solution of 3.0 g of the compound of Formula I in 6 mL of acetone at room temperature, 0.7 g of citraconic Acid is added. After stirring at room temperature overnight, the corresponding salt is isolated by filtration as a white solid with a 86:14 rotamer ratio.

Example 23

2,2-Dimethyl Malonic Acid Salt of the Compound of Formula I (87:13)

To a solution of 3.0 g of the compound of Formula I in 11 mL of THF at room temperature, 0.7 g of 2,2-dimethyl malonic acid is added. After stirring at room temperature overnight, the corresponding salt is isolated by filtration as a white solid with a 87:13 rotamer ratio.

Example 24

Meso-2,3-dimethyl Succinic Acid Salt of the Compound of Formula I (88:12)

To a solution of 3.0 g of the compound of Formula I in 10 mL of methanol at room temperature, 0.79 g of meso-2,3-dimethyl succinic acid is added. After stirring at room temperature overnight, the corresponding salt is isolated by filtration as a white solid with a 88:12 rotamer ratio.

Example 25

2,2-Dimethyl-succinic Acid Salt of the Compound of Formula I (91:9)

To a solution of 3.0 g of the compound of Formula I in 6 mL of methanol at room temperature, 0.78 g of 2,2-dimethyl-succinic acid is added. After stirring at room temperature overnight, the corresponding salt is isolated by filtration as a white solid with a 91:9 rotamer ratio.

Example 26

Dibenzoyl-D-tartaric Acid Salt ("DBTA") of the Compound of Formula I

To a solution of the compound of Formula I (6.0 g, 10.8 mmol) in of acetone (200 mL) was added dibenzoyl-D-tartaric acid (3.6 g, 9.6 mmol) dissolved in acetone (50 mL). The resulting reaction mixture was stirred for 16 hours at 25° C., the solids were filtered and washed twice with acetone (25 mL). The isolated yield was 55–65%. The solids were >95% of rotamer 1 by HPLC. $^1$H NMR (400 MHz, D$_2$O, mixture of diastereomers) δ 8.3 (d, J=6.6 Hz, 1H), 8.1 (d, J=7.6 Hz, 4H),7.7 (m, overlapping, 4H), 7.6 (t, J=7.6 Hz, 4H), 7.4 (d, J=6.6 Hz, 1H), 7.2 (d, J=7.3 Hz, 2H), 4.6 (br, unresolved m, 1H), 4.0 (q, J=7.0 Hz, 2H), 3.7 to 3.1 (br, overlapping unresolved, m, 3H), 3.4 to 3.1 (br, overlapping, 5H), 2.9 (m, 3H), 2.4 (s, 3H), 2.3 (s, 3H), 2.2 to 1.8 (br, overlapping, 8H), 1.5 (s, 3H), 1.2 (t, J=7.0 Hz, 3H); M.P. 179.8° C.

HRMS calcd for C$_{28}$H$_{37}$BrN$_4$O$_3$ 557.2127. found 557.2131.

Example 27

Dibenzoyl-L-tartaric Acid Salt of the Compound of Formula I

To a solution of the compound of Formula I (6.0 g, 10.8 mmol) in 200 mL of acetone was added dibenzoyl-L-tartaric acid (3.6 g, 9.6 mmol) dissolved in acetone (50 mL). The resulting reaction mixture was stirred for 16 hours at 25° C., the solids were filtered and washed twice with acetone (25 mL). The isolated yield was 55–65%. The solids were >95% of rotamer 2 by HPLC. $^1$H NMR (400 MHz, D$_2$O, mixture of diastereomers) δ 8.3 (d, J=6.6 Hz, 1H), 8.1 (d, J=7.6 Hz, 4H), 7.7 (m, overlapping, 4H), 7.6 (t, J=7.6 Hz, 4H), 7.4 (d, J=6.6 Hz, 1H), 7.2 (d, J=7.3 Hz, 2H), 4.6 (br, unresolved m, 1H), 4.0 (q, J=7.0 Hz, 2H), 3.7 to 3.1 (br, overlapping unresolved, m, 3H), 3.4 to 3.1 (br, overlapping, 5H), 2.9 (m, 3H), 2.4 (s, 3H), 2.3 (s, 3H), 2.2 to 1.8 (br, overlapping, 8H), 1.5 (s, 3H), 1.2 (t, J=7.0 Hz, 3H); M.P. 179.1° C.

HRMS calcd for C$_{28}$H$_{37}$BrN$_4$O$_3$ 557.2127. found 557.2131.

Example 28

Glutaric Acid Salt of the Compound of Formula I (93:7)

To a solution of 3.0 g of the compound of Formula I in 6 mL of methanol at room temperature, 0.7 g of glutaric acid is added. After stirring at room temperature overnight, the corresponding salt is isolated by filtration as a white solid with a 93:7 rotamer ratio.

Example 29

4-Hydroxybenzoic Acid Salt (2:98)

To an agitated solution of 10 g of the compound of Formula I free base in 100 mL of isopropyl acetate was added a solution of 2.5 g of 4-hydroxybenzoic acid in 50 mL of EtOH. The mixture was heated to 65 C until a clear solution was obtained. After cooling to room temperature, the mixture was filtered to afford white solids with a 2:98 rotamer ratio.

Example 30

Malonic Acid Salt of the Compound of Formula I (82:18)

To a solution of 3.0 g of the compound of Formula I in 12 mL of THF at room temperature, 0.57 g of malonic acid is added. After stirring at room temperature overnight, the corresponding salt is isolated by filtration as a white solid with a 82:18 rotamer ratio.

Example 31

(R)-Methyl-succinic Acid Salt of the Compound of Formula I (82:18)

To a solution of 2.0 g of the compound of Formula I in 5 mL of acetone at room temperature, 0.47 g of (R)-methyl-succinic acid is added. After stirring at room temperature overnight, the corresponding salt is isolated by filtration as a white solid with a 82:18 rotamer ratio.

Example 32

2-Methylglutaric Acid Salt of the Compound of Formula I (2:98)

To a solution of 3.0 g of the compound of Formula I in 11 mL of acetonitrile at room temperature, 0.78 g of 2-methylglutaric acid is added. After stirring at room temperature overnight, the corresponding salt is isolated by filtration as a white solid with a 2:98 rotamer ratio.

Example 33

3-Methylglutaric Acid Salt of the Compound of Formula I (90:10)

To a solution of 3.0 g of the compound of Formula I in 12 mL of acetonitrile at room temperature, 0.78 g of 3-methylglutaric acid is added. After stirring at room temperature overnight, the corresponding salt is isolated by filtration as a white solid with a 90:10 rotamer ratio.

Example 34

1,5-Naphthalenedisulfonic Acid Salt (1:1 Salt) of the Compound of Formula I (4:96)

To a solution of 1.0 g of the compound of Formula I in 10 mL of acetonitrile at 45° C., 0.5 g of 1,5-naphthalenedisulfonic acid in 10 mL MeOH is added. After stirring at reflux for 1 hour, the solution is cooled to room temperature. The corresponding salt is isolated by filtration as a white solid with a 4:96 rotamer ratio.

Determination of the Rotamer Ratio using HPLC: The rotamer ratio is determined by injection of a sample of salt dissolved in cold water into a HPLC (215 nm detector, YMC-Pack pro-C-18, 250×4.6 mm, 4 mcm, 25–30° C., using mobile phases A: 10%CH$_3$CN: 90% 10 mM Potassium hydrogen phosphate (pH 6.2) and B: 80%CH$_3$CN: 20% 10 mM Potassium hydrogen phosphate (pH 6.2); under the gradient conditions of 0 mins 70%A: 30%B; 25 mins 70%A: 30%B; 40 mins 0%A: 100%B) column. For a typical benzene sulfonate salt, the rotamers 1 and 2 were found to have retention times of about 14.2 minutes while the rotamers 3 and 4 were found to have retention times of about 16.5 minutes.

TABLE 1

| Salt | Solvent (diastereomeric ratio 1,2 to 3,4 in solids) | | | | | |
|---|---|---|---|---|---|---|
| 1. Acetate | MTBE/ Heptane (5:95) | | | | | |
| 2. Benzene sulfonate | Acetone (4:96) | MTBE (7:93) | THF (80:20) | Toluene (95:5) | Acetonitrile (95:5) | Water (95:5) |
| 3. Bromide | ACN (1:1) (75:25) | | | | | |
| 4. Camsylate | MTBE (57:43) at rt | | | | | |
| 5. Citrate | EtOH, (97:3) | ACN/MeOH 40:60) | | | | |
| 6. Dihydrochloride | EtOH (80:20) | | | | | |
| 7. Esylate | EtOH (70:30) | | | | | |
| 8. Fumarate | Acetone (93:7) | ACN (94:6) | MeOH: (97:3) EtOH:(97:3) iPrOH: (9:1) | | | |
| 9. Hydrobromide | ACN/IPA (73:27) | | | | | |
| 10 Hydrochloride | MTBE (95:5) | Acetone (95:5) | ACN (95:5) | EtOH (95:5 | | |
| 11 Hydroxynaphthoate | MTBE (82:18) | | | | | |
| 12 Iodide (TMSl/EtOH) | ACN/MTBE (54:46) | | | | | |
| 13 Isethionate | EtOH (95:5) | | | | | |
| 14 Lactate | MTBE (8:1) | EtOAc, (9:1) | MTBE (87:13) | | | |
| 15 Malate | Acetone/ EtOH | Acetone (93:7) | | | | |
| 16 Maleate | MTBE (96:4) | ACN/ MeOH (22:78) | | | | |
| 17 Mandelate | THF (94:6) | Acetone (94:6) | ACN (93:7) | | | |
| 18 Mesylate | ACN (94:6) | | | | | |
| 19 Mucate | MeOH (1:1) | | | | | |
| 20 Pamoate | CHCl3 (40:60) | Water (Na salt + Y.HCl) (1:1) | | | | |
| 21 Salicylate | EtOAc/ water (6:1) | EtOH (95:5) stable | iPrOAc, (95:5) stable | | | |
| 22 Succinate | MeOH (83:17) | EtOH, (80:20) | | | | |

TABLE 1-continued

| Salt | Solvent (diastereomeric ratio 1,2 to 3,4 in solids) | | | |
|---|---|---|---|---|
| 23 Sulfate | ACN(41:59) | | | |
| 24 5-Sulfo salicylate | Acetone (97:3) | | | |
| 25 (L)-Tartarate | THF (41:59) | | | |
| 26 Terephthalate | EtOH (90:10) | | | |
| 27 Tosylate | THF (99:1) | Acetone (7:93) | ACN (97:3) | IPA (91:9) |
| 28 t-Aconitic acid salt | EtOH (91:9) | | | |
| 29 cis-Aconitic acid salt | EtOH (58:42) | | | |
| 30 (D)-camphorate | Acetone, 3:97 | ACN, 3:97 | MeOH, 3:97 | |
| 31 (L)-Camphorate | Acetone, 3:97 | ACN, 3:97 | MeOH, 3:97 | |
| 32 1,2-cis-cyclo-hexanedi-carboxylate | THF (78:22) | | | |
| 33 1,2-trans-cyclo-hexanedi-carboxylate | THF (83:17) | | | |
| 34 (R)-citramalate | MeOH (77:23) | | | |
| 35 Citraconate | Acetone (86:14) | ACN (82:18) | | |
| 36 2,2-dimethyl glutarate | ACN (97:3) | | | |
| 37 3,3-dimethyl glutarate | ACN (97:4) | | | |
| 38 2,2-dimethyl malonate | THF (87:13) | | | |
| 39 2,3-Dimethyl succinate | MeOH (88:12) | | | |
| 40 2,2Dimethyl succinate | MeOH, (91:9) | | | |
| 41 (D)-DBTA | Acetone only peak 1 (95%) | ACN only peak 1 (95%) | MeOH only peak 1 (95%) | |
| 42 (L)-DBTA | Acetone only peak 2 (91%) | ACN only peak 2 (91%) | MeOH only peak 2 (91%) | |
| 43 Glutarate | EtOH (93:7) | MTBE (92:8) | | |
| 44 4-Hydroxy benzoate | iPrOAc (4:96) | iPrOAc (2:98) | | |
| 45 4-Hydroxy-2-naphthoate | iPrOAc (18:82) | | | |
| 46 Malonate | THF (82:18) | THF (88:12) | | |
| 47 (R)-methyl succinate | Acetone, (82:18) | | | |
| 48 2-methyl glutarate | ACN (90:10) | | | |
| 49 3-methyl glutarate | ACN (2:98) | | | |
| 50 Napadisylate (1,5)- | Acetone/MeOH (8:92) | ACN/MeOH (4:96) | MeOH/EtOH (7:93) | MeOH (5:95) |
| 51 Saccharin | Acetone, (95:5) | | | |
| 52 Sulfamic acid | [2 eq acid] ACN (55:45) | [2 eq acid] EtOAc (55:45) | | |

While the EXAMPLES and TABLE 1 are described herein as the preparation of the diastereomeric pairs of the salt of the compound of Formula I, it will be apparent to those skilled in the art that many modifications, variations and alterations to the present disclosure, both to materials, methods and reaction conditions, may be practiced. All such modifications, variations and alterations are intended to be within the spirit and scope of the present invention.

What is claimed is:

1. A process for preparing a mixture of rotamers or rotamer pairs of a salt of a basic compound of Formula I:

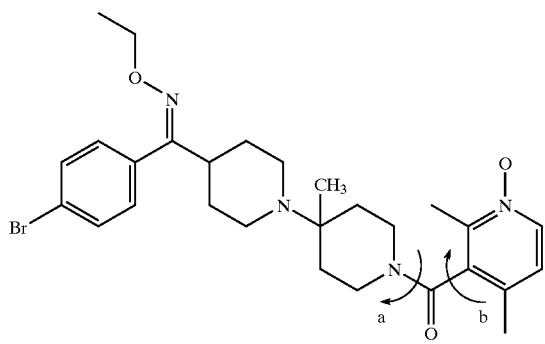

Formula I wherein said mixture comprises either
(i) the 1-rotamer in a higher molar percent than the 2-rotamer of said salt, or
(ii) the 2-rotamer in a higher molar percent than the 1-isomer of said salt, or
(iii) the 1,2-rotamer pair in a higher molar percent than the 3,4-rotamer pair of said salt, or
(iv) the 3,4-rotamer pair in a higher molar percent than the 1,2-rotamer pair of said salt, said process comprising reacting said basic compound with an acid in admixture with a solvent wherein said solvent is a ketone, ether, hydrocarbon or mixtures thereof, with said solvent being used in a ratio about 15:1 with respect to said basic compound, further wherein said 1-rotamer (structure A), 2-rotamer (structure B), 3-rotamer (structure C) and 4-rotamer (structure D) elute in the order 1, 2, 3 and 4 from a chiral HPLC column, and are shown by their following diastereomeric structures due to restricted rotation of bonds marked a and b in Formula I:

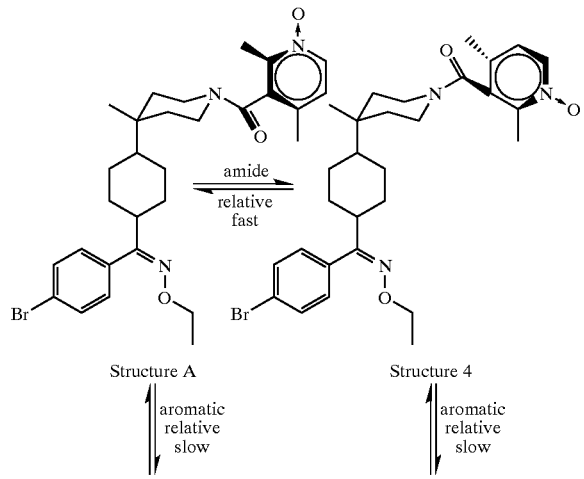

-continued

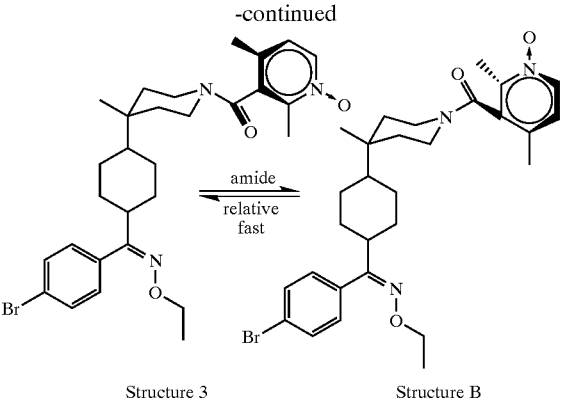

2. The process of claim 1, wherein said molar percent is 45:55 of the concentration of each rotamer over its corresponding rotamer as described in (i) and (ii), or of each rotamer pair over its corresponding rotamer pair as described in (iii) and (iv) of the salt.

3. The process of claim 2, wherein said molar percent is 25:75 of the concentration of each rotamer over its corresponding rotamer as described in (i) and (ii), or of each rotamer pair over its corresponding rotamer pair as described in (iii) and (iv) of the salt.

4. The process of claim 3, wherein said molar percent is 10:90 of the concentration of each rotamer over its corresponding rotamer as described in (i) and (ii), or of each rotamer pair over its corresponding rotamer pair as described in (iii) and (iv of the salt.

5. The process at claim 1, wherein said basic compound is a pharmaceutical compound.

6. The process of claim 2, wherein said acid is a pharmaceutically useful acid.

7. The process of claim 1, wherein said acid is used in a ratio about 1:1 with respect to said basic compound.

8. The process of claim 1, wherein said salt is selected from the group consisting of benzene sulfonate, naphthalene-1,5-disulfonate, maleate, (D)-camphorate, (L)-camphorate, 2-methyl glutarate, 3-methyl glutarate, 4-hydroxy benzoate, p-toluene sulfonate, dibenzoyl-D-tartarate, dibenzoyl-L-tartarate, fumarate, hydrochloride and hydrobromide.

9. The process of claim 8, wherein said salt is benzene sulfonate.

10. The process of claim 1, wherein said ketone is selected from the group consisting of acetone, methyl ethyl ketone, methyl n-amyl ketone and mixtures thereof.

11. The process of claim 10, wherein said ketone is acetone.

12. The process of claim 1, wherein said ether is selected from the group consisting of tetrahydrofuran, diglyme, methyl ethyl ether and mixtures thereof, and said hydrocarbon is selected from the group consisting of toluene, xylene, chlorobenzene, hexane, heptane and mixtures thereof.

13. The process of claim 9, wherein said benzene sulfonate is formed at about 25–70° C.

14. The process of claim 8, wherein said salt is dibenzoyl tartarate.

15. The process of claim 14, wherein said dibenzoyl tartarate is prepared by reacting the compound of Formula I with dibenzoyl tartaric acid in a ketone solvent.

16. The process of claim 15, wherein said dibenzoyl tartaric acid is the (D) acid.

17. The process of claim 15, wherein said dibenzoyl tartaric acid is the acid.

18. The process of claim 8, wherein said salt is p-toluene sulfonate.

19. The process of claim 18, said p-toluene sulfonate is prepared by reacting said compound of Formula I with p-toluene sulfonic acid in an ether solvent.

20. The process of claim 19, wherein said ether is tetrahydrofuran.

21. The process of claim 19, wherein p-toluene sulfonate is prepared by reacting said compound of Formula I with p-toluene sulfonic acid in a ketone solvent.

22. The process of claim 21, wherein said ketone is acetone.

23. A process for preparing a mixture of rotamers or rotamer pairs of the benzene sulfonate salt of a compound of Formula I:

Formula I

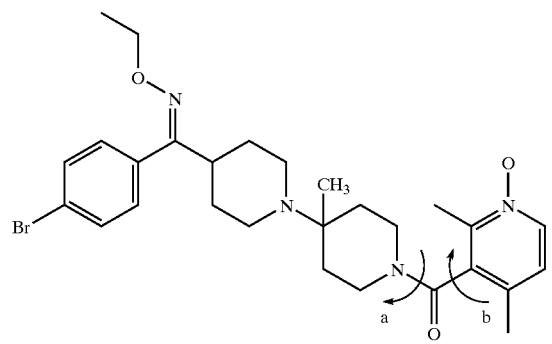

wherein said mixture comprises either (i) the 1-rotamer of said benezenesulfonate salt in a higher molar percent than the 2-rotamer, or (ii) the 2-rotamer of said benezenesulfonate salt in a higher molar percent than the 1-isomer, or (iii) the 1,2-rotamer pair of said benezenesulfonate salt in a higher molar percent than the 3,4-rotamer pair, or (iv) the 3,4-rotamer pair of said benezenesulfonate salt in a higher molar percent than the 1,2-rotamer pair, said process comprising:

(a) preparing a first intimate mixture of said compound of Formula I in a solvent;

(b) maintaining said first intimate mixture at about 25–70° C.;

(c) preparing a second intimate mixture of benzene sulfonic acid in the same solvent stated in step (a);

(d) combining said first intimate mixture and said second intimate mixture to prepare a combined mixture and maintaining the combined mixture at about 25–70° C. to induce formation of the benzene sulfonate salt; and (e) isolating the benzene sulfonate salt wherein said solvent is a ketone, ether, hydrocarbon or mixtures thereof, with said solvent being used in a ratio about 15:1 with respect to said basic compound, further wherein said 1-rotamer (structure A), 2-rotamer (structure B), 3-rotamer (structure C) and 4-rotamer (structure D) elute in the order 1, 2, 3 and 4 from a chiral HPLC column, and are shown by their following diastereomeric structures due to restricted rotation of bonds marked a and b in Formula I:

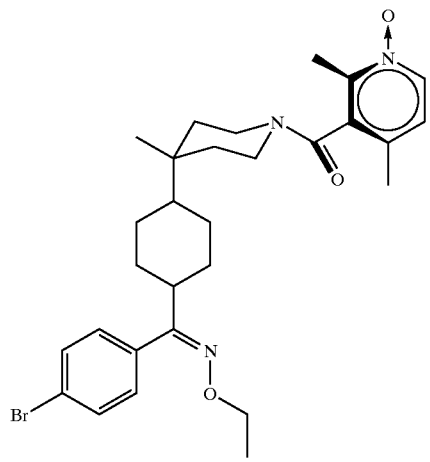

Structure A aromatic
relative
slow

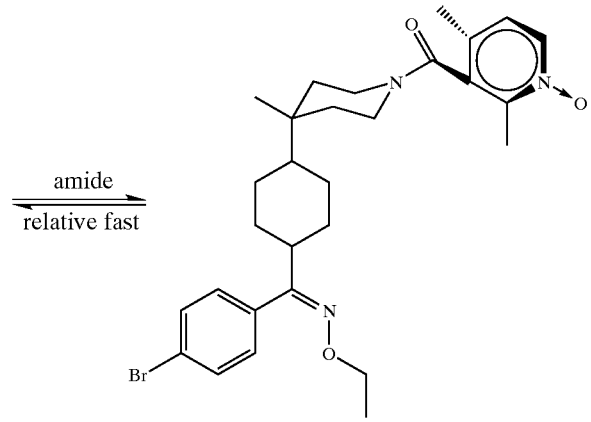

Structure 4 amide
relative fast aromatic
relative
slow

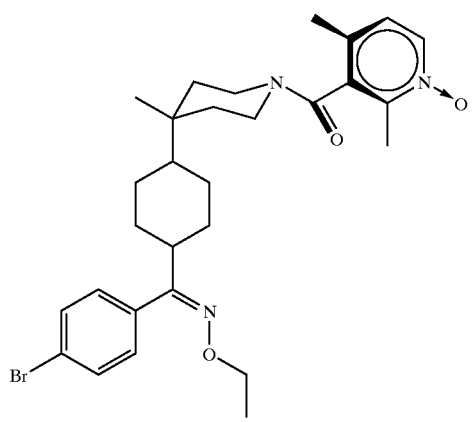

Structure 3

⇌ amide relative fast

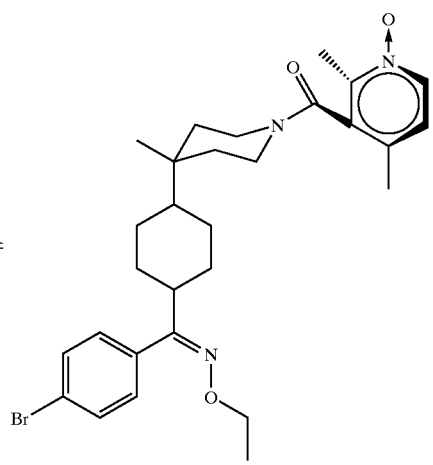

Structure B

24. The process of claim 23, wherein said molar percent is 45:55 of the concentration of each rotamer of the benzene sulfonate salt over its corresponding rotamer as described in (i) and (ii), or of each rotamer pair of the benzene sulfonate salt over its corresponding rotamer pairs described in (iii) and (iv).

25. The process of claim 23, wherein said molar percent is 25:75 of the concentration of each rotamer of the benzene sulfonate salt over its corresponding rotamer as described in (i) and (ii), or of each rotamer pair of the benzene sulfonate salt over its corresponding rotamer pair as described in (iii) and (iv).

26. The process of claim 23, wherein said molar percent is 5:95 of the concentration of each rotamer of the benzene sulfonate salt over its corresponding rotamer as described in (i) and (ii), or of each rotamer pair of the benzene sulfonate salt over its corresponding rotamer pair as described in (iii) and (iv).

27. The process of claim 23, wherein said ketone is selected from the group consisting of acetone, methyl ethyl ketone, methyl n-amyl ketone and mixtures thereof.

28. The process of claim 27, said ketone is acetone.

29. The process of claim 23, wherein said ether is selected from the group consisting of tetrahydrofuran, diglyme, methyl ethyl ether and mixtures thereof, and said hydrocarbon is selected from the group consisting of toluene, xylene, chlorobenzene, hexane, heptane and mixtures thereof.

30. A mixture of rotamers or rotamer pairs of a salt of a basic compound wherein said mixture comprises either (i) the 1-rotamer of said salt in a higher molar percent than the 2-rotamer, or (ii) the 2-rotamer of said salt in a higher molar percent than the 1-isomer, or (iii) the 1,2-rotamer pair of said salt in a higher molar percent than the 3,4-rotamer pair, or (iv) the 3,4-rotamer pair of said salt in a higher molar percent than the 1,2-rotamer pair said mixture prepared by a process comprising reacting said basic compound with an acid in admixture with a solvent, further wherein said basic compound is the compound of Formula I:

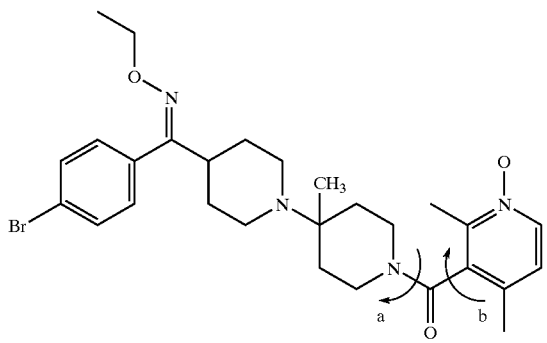

Formula I said acid is benzene sulfonic acid, said salt is benzene sulfonate, and said molar percent is 45:55 of said rotamer or rotamer pair as described in (i), (ii), (iii) and (iv), wherein said solvent is a ketone, ether, hydrocarbon or mixtures thereof, with said solvent being used in a ratio about 15:1 with respect to said basic compound, further wherein said 1-rotamer (structure A), 2-rotamer (structure B), 3-rotamer (structure C) and 4-rotamer (structure D) elute in the order 1, 2, 3 and 4 from a chiral HPLC column, and are shown by their following diastereomeric structures due to restricted rotation of bonds marked a and b in Formula I:

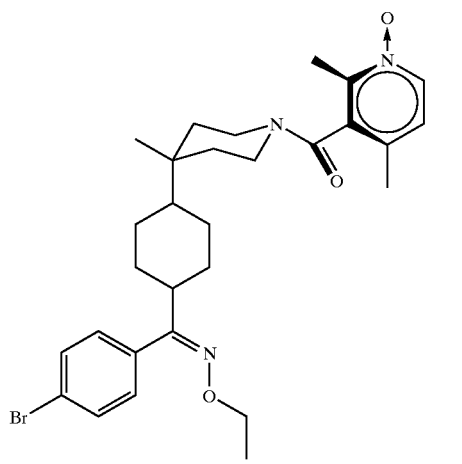

Structure A

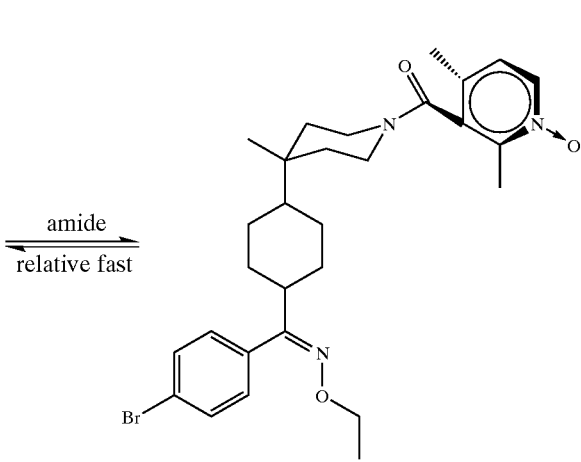

Structure 4

⇌ amide relative fast

⇅ aromatic relative slow (left side)

⇅ aromatic relative slow (right side)

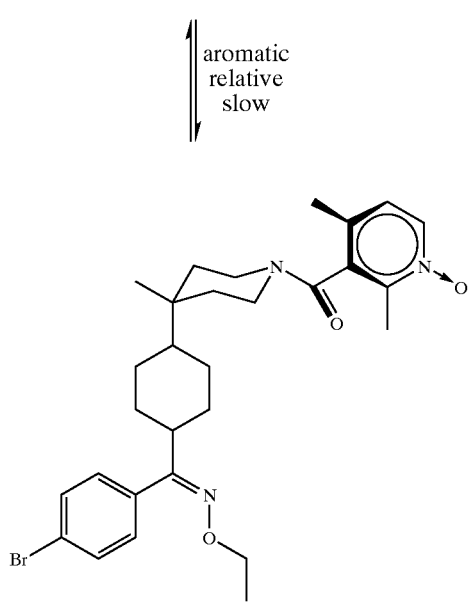

Structure 3

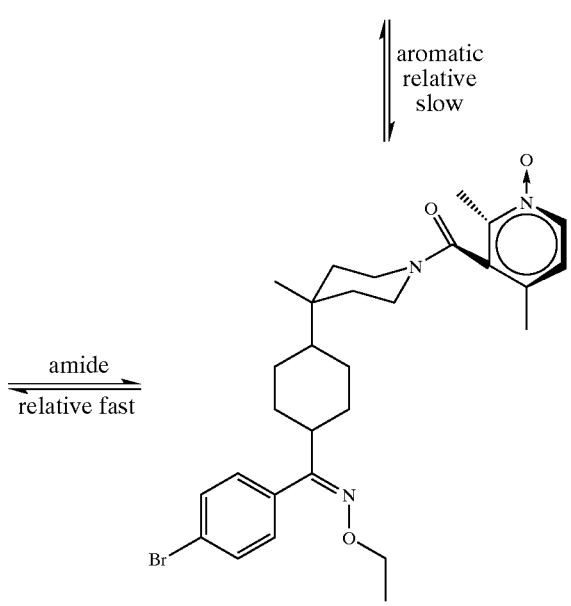

Structure B

⇌ amide relative fast

31. An acid salt of a basic compound, wherein said basic compound has the formula:

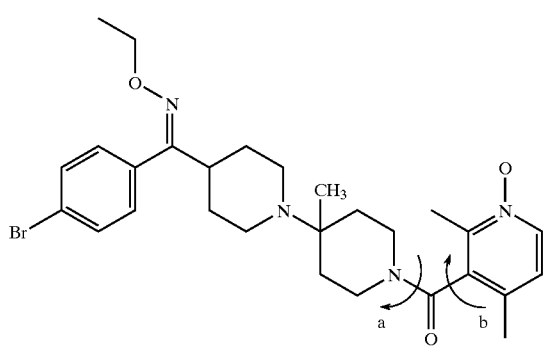

Formula I and wherein said acid salt is selected from the group consisting of acetate, benzenesulfonate, benzoate, bicarbonate, bromide, calcium edetate, camphorsulfonate, carbonate, chloride/dihydrochloride, citrate, N,N-di(dehydroabietyl)ethylenediamine, edetate, 1,2-ethanedisulfonate, ethanesulfonate, fumarate, glucoheptonate, gluconate, glutamate, p-glycollamidophenylarsonate, hexylresorcinate, hyclate, hydrobromide, hydrochloride, 2-hydroxyethanesulfonate, hydroxynaphthoate, iodide, lactate, lactobionate, lauryl sulfonate, malate, maleate, mandelate, methanesulfonate, methylbromide, methylnitrate, methylsulfate, mucate, nafate, napsylate, nitrate, pamoate, pantothenate, phosphate/diphosphate, polygalacturonate, salicyclate, sodium succinate, stearate, subacetate, succinate, sulfate, tosylate, tannate, tartarate/bitartarate, 8-chlorotheophyllinate, triethiodide, adipate, alginate, aminosalicyclate, anhydromethylenecitrate, arecoline, asparate, bisulfate, butylbromide, camphorate, digluconate, dihydrobromide, disuccinate, glycerophosphate, hemisulfate, hydrofluoride, hydrotodide, methylenebis(salicyclate), naphthalenedisulfoflate, oxalate, pectinate, persulfate, phenylethylbarbiturate, picrate, propionate, thiocyanate, undecanoate, acetylaminoacetate, N-acetyl-L-asparaginate, N-acetylcystinate, adamantoate, adipoate, N-alkylsulfamates, anthraquinone-1,5-disulfonate, arabolactansulfate, argininate, aspartate, betaine, carnitine, 4-chloro-m-toluenesulfonate, decanoate, diacetyl sulfate, dibenzylethylenediamine, dimethylamine, diguaiacylphosphate, dioctylsulfosuccinate, pamoate, fructose-1,6-diphosphate, glucose phosphate, L-glutaminate, hydroxynaphthoate, lauryl sulfate, lysine, 2-naphthenesulfonate, octanonate, tannate and theobromine acetate, further wherein said acid salt exists as a mixture of rotamers or rotamer pairs with said mixture comprising either (i) the 1-rotamer of said salt in a higher molar percent than the 2-rotamer, or
(ii) the 2-rotamer of said salt in a higher molar percent than the 1-isomer, or
(iii) the 1,2-rotamer pair of said salt in a higher molar percent than the 3,4-rotamer pair, or
(iv) the 3,4-rotamer pair of said salt in a higher molar percent than the 1,2-rotamer pair, further wherein said 1-rotamer (structure A), 2-rotamer (structure B), 3-rotamer (structure C) and 4-rotamer (structure D) elute in the order 1, 2, 3 and 4 from a chiral HPLC column, and are shown by their following diastereomeric structures due to restricted rotation of bonds marked a and b in Formula I:

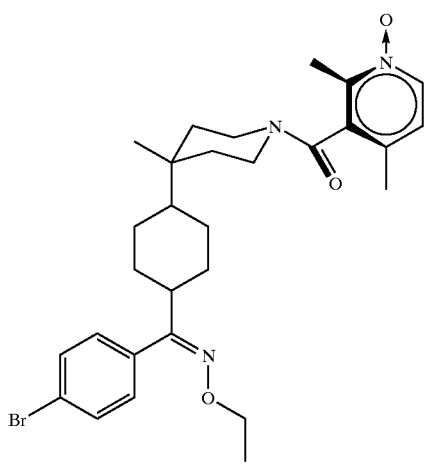

Structure A

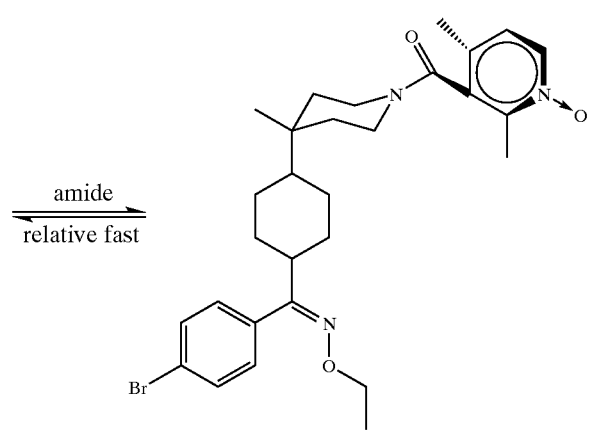

Structure 4

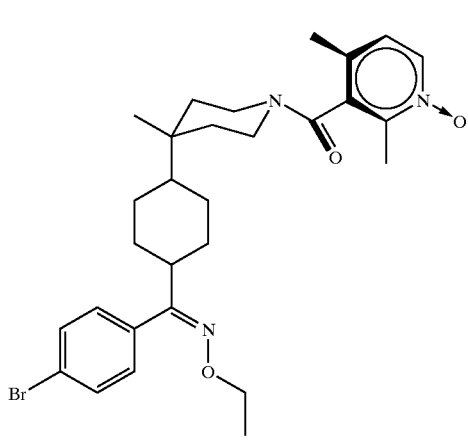

Structure 3

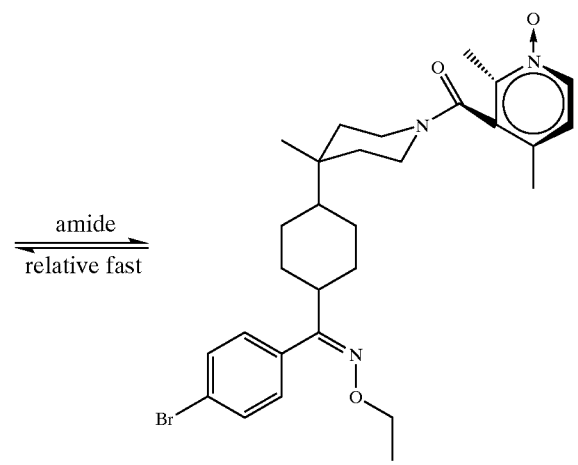

Structure B

32. A fumarate salt of a basic compound, wherein said basic compound has the formula:

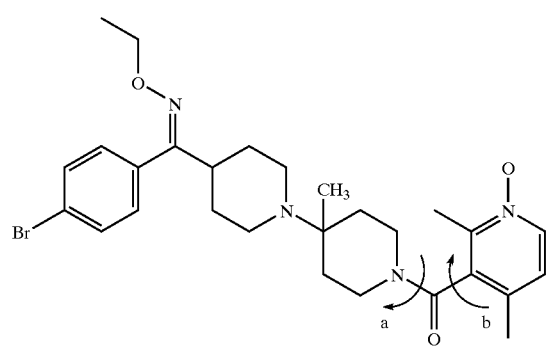

Formula I wherein said salt exists as a mixture of rotamers or rotamer pairs with said mixture comprising either (i) the 1-rotamer of said salt in a higher molar percent than the 2-rotamer, or (ii) the 2-rotamer of said salt in a higher molar percent than the 1-isomer, or (iii) the 1,2-rotamer pair of said salt in a higher molar percent than the 3,4-rotamer pair, or (iv) the 3,4-rotamer pair of said salt in a higher molar percent than the 1,2-rotamer pair, further wherein said 1-rotamer (structure A), 2-rotamer (structure B), 3-rotamer (structure C) and 4-rotamer (structure D) elute in the order 1, 2, 3 and 4 from a chiral HPLC column, and are shown by their following diastereomeric structures due to restricted rotation of bonds marked a and b in Formula I:

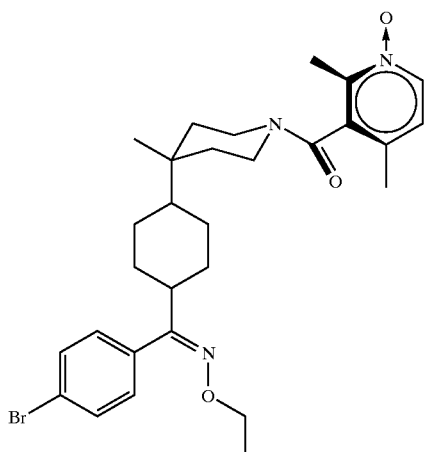

Structure A

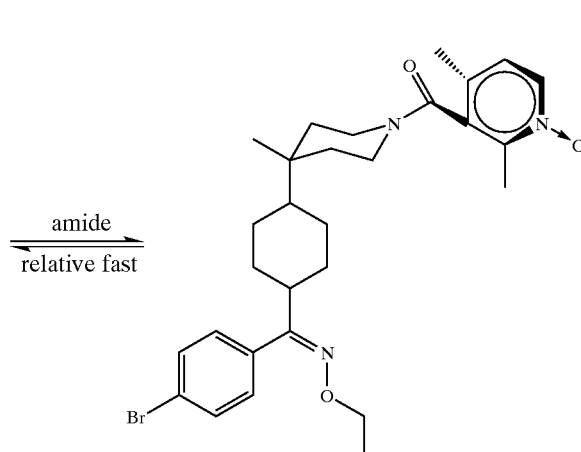

Structure 4 amide
relative fast aromatic
relative
slow

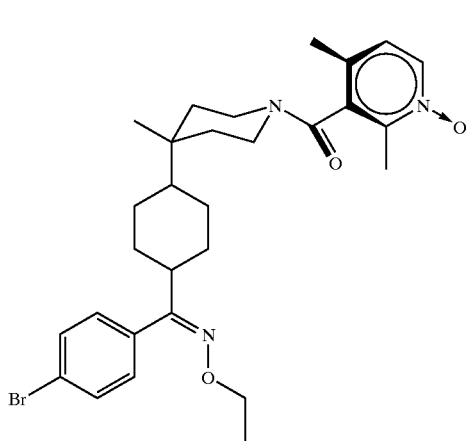

Structure 3

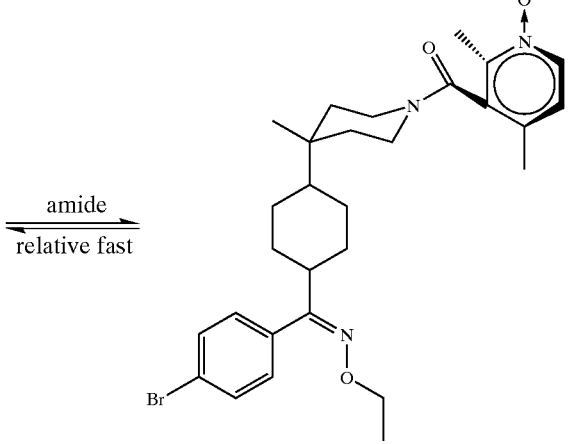

Structure B amide
relative fast aromatic
relative
slow

33. A (D)-camphorate salt of a basic compound, wherein said basic compound has the formula:

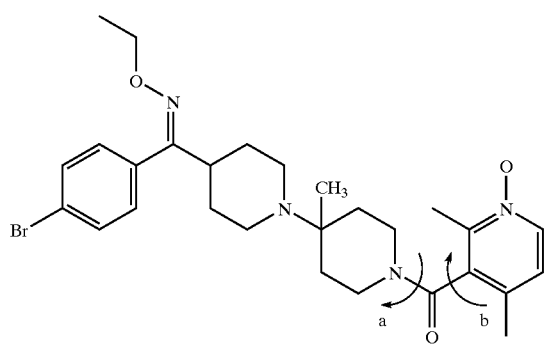

Formula I wherein said salt exists as a mixture of rotamers or rotamer pairs with said mixture comprising either (i) the 1-rotamer of said salt in a higher molar percent than the 2-rotamer, or (ii) the 2-rotamer of said salt in a higher molar percent than the 1-isomer, or (iii) the 1,2-rotamer pair of said salt in a higher molar percent than the 3,4-rotamer pair, or (iv) the 3,4-rotamer pair of said salt in a higher molar percent than the 1,2-rotamer pair, further wherein said 1-rotamer (structure A) 2-rotamer (structure B), 3-rotamer (structure C) and 4-rotamer (structure D) elute in the order 1, 2, 3 and 4 from a chiral HPLC column, and are shown by their following diastereomeric structures due to restricted rotation of bonds marked a and b in Formula I:

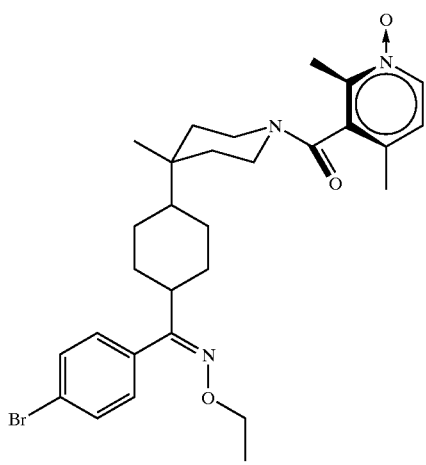

Structure A

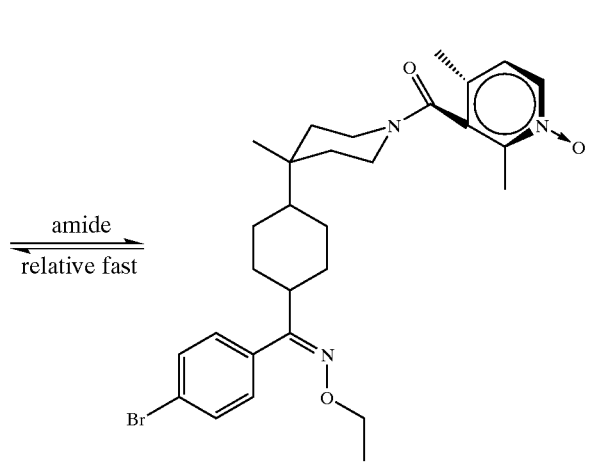

Structure 4

⇅ aromatic relative slow

⇅ aromatic relative slow

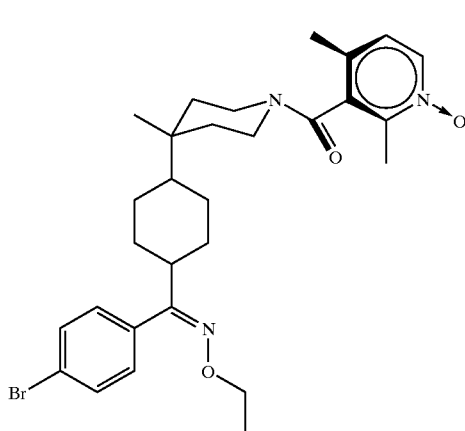

Structure 3

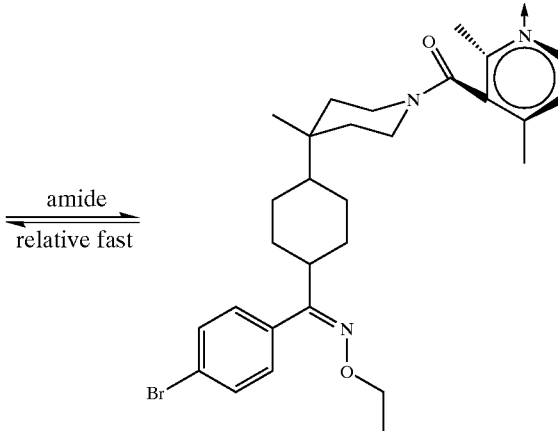

Structure B

34. A benzene sulfonate salt of a basic compound, wherein said basic compound has the formula:

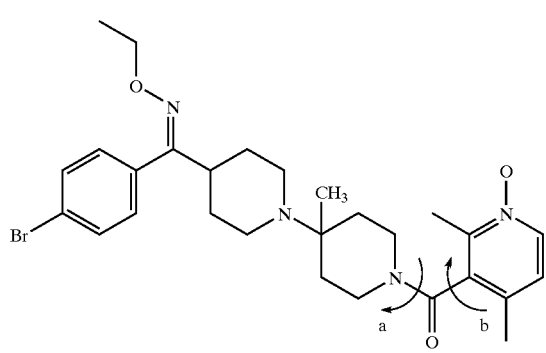

Formula I wherein said salt exists as a mixture of rotamers or rotamer pairs with said mixture comprising either (i) the 1-rotamer of said salt in a higher molar percent than the 2-rotamer, or (ii) the 2-rotamer of said salt in a higher molar percent than the 1-isomer, or (iii) the 1,2-rotamer pair of said salt in a higher molar percent than the 3,4-rotamer pair, or (iv) the 3,4-rotamer pair of said salt in a higher molar percent than the 1,2-rotamer pair, further wherein said 1-rotamer (structure A), 2-rotamer (structure B), 3-rotamer (structure C) and 4-rotamer (structure D) elute in the order 1, 2, 3 and 4 from a chiral HPLC column, and are shown by their following diastereomeric structures due to restricted rotation of bonds marked a and b in Formula I:

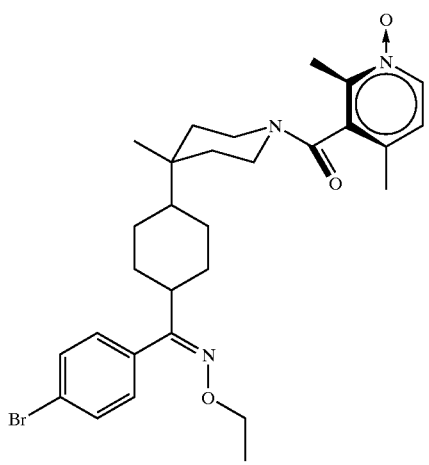

Structure A

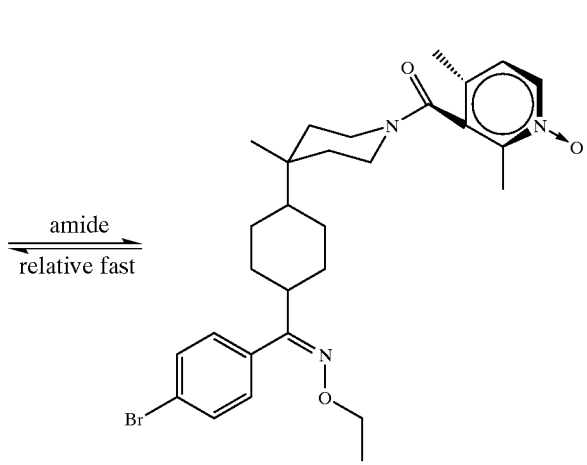

Structure 4

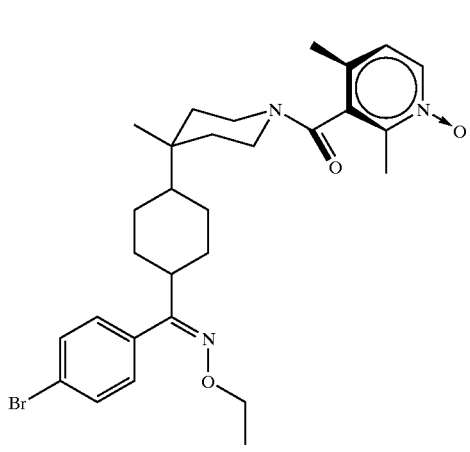

Structure 3

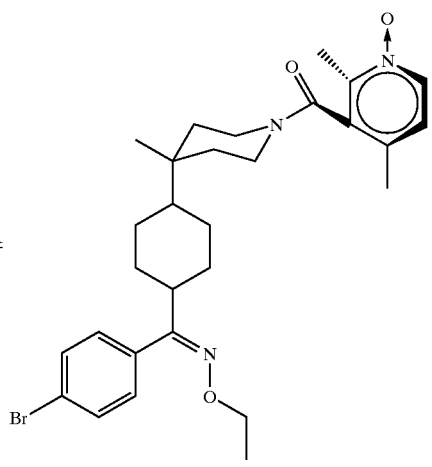

Structure B

35. A (L)-camphorate salt of a basic compound, wherein said basic compound has the formula:

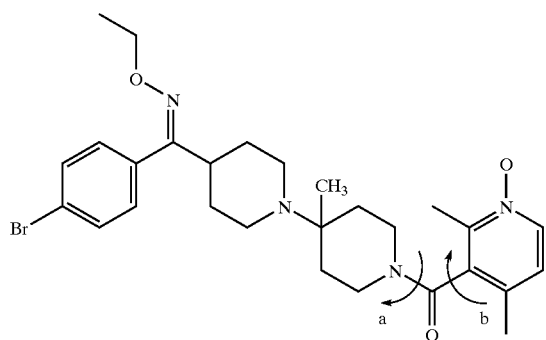

Formula I wherein said salt exists as a mixture of rotamers or rotamer pairs with said mixture comprising either (i) the 1-rotamer of said salt in a higher molar percent than the 2-rotamer, or (ii) the 2-rotamer of said salt in a higher molar percent than the 1-isomer, or (iii) the 1,2-rotamer pair of said salt in a higher molar percent than the 3,4-rotamer pair, or (iv) the 3,4-rotamer pair of said salt in a higher molar percent than the 1,2-rotamer pair, further wherein said 1-rotamer (structure A), 2-rotamer (structure B), 3-rotamer (structure C) and 4-rotamer (structure D) elute in the order 1, 2, 3 and 4 from a chiral HPLC column, and are shown by their following diastereomeric structures due to restricted rotation of bonds marked a and b in Formula I:

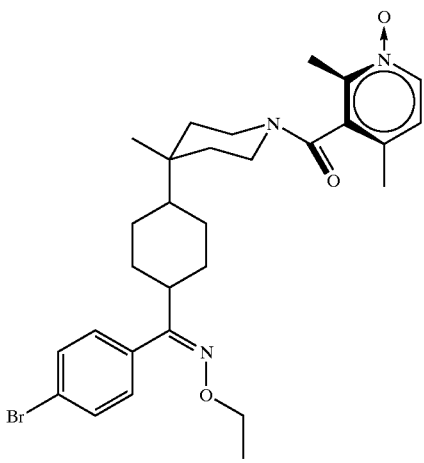

Structure A

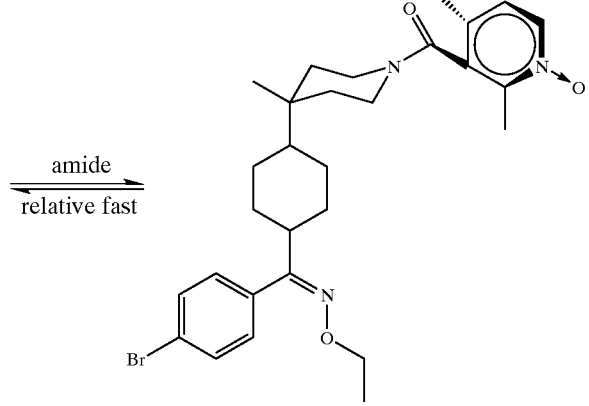

Structure 4

⇌ amide relative fast

⇅ aromatic relative slow

⇅ aromatic relative slow

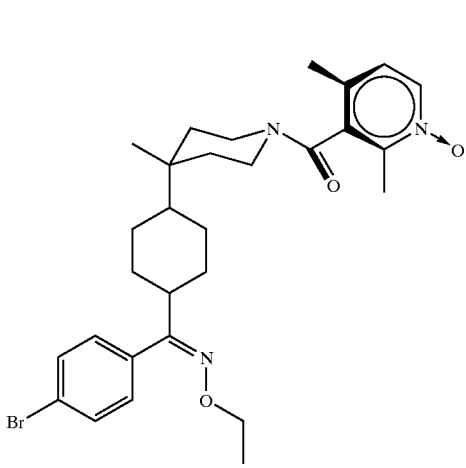

Structure 3

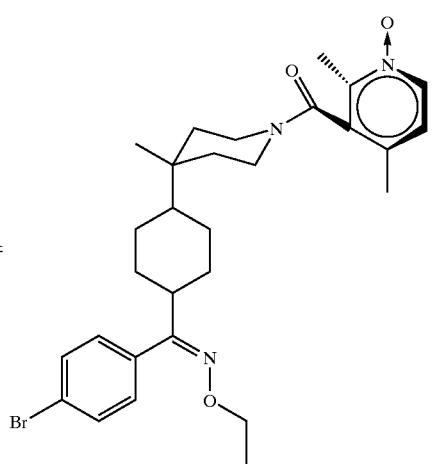

Structure B

⇌ amide relative fast

36. A dibenzoyl-(D)-tartarate salt of a basic compound, wherein said basic compound has the formula:

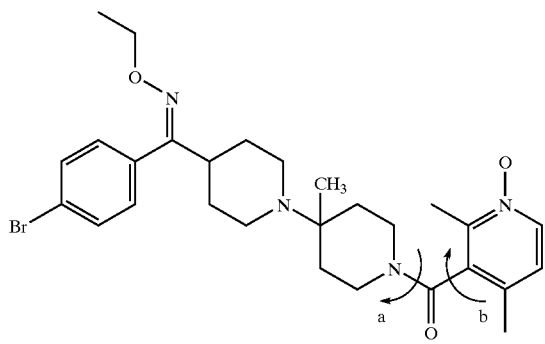

Formula I wherein said salt exists as a mixture of rotamers or rotamer pairs with said mixture comprising either (i) the 1-rotamer of said salt in a higher molar percent than the 2-rotamer, or (ii) the 2-rotamer of said salt in a higher molar percent than the 1-isomer, or (iii) the 1,2-rotamer pair of said salt in a higher molar percent than the 3,4-rotamer pair, or (iv) the 3,4-rotamer pair of said salt in a higher molar percent than the 1,2-rotamer pair, further wherein said 1-rotamer (structure A), 2-rotamer (structure B), 3-rotamer (structure C) and 4-rotamer (structure D) elute in the order 1, 2, 3 and 4 from a chiral HPLC column, and are shown by their following diastereomeric structures due to restricted rotation of bonds marked a and b in Formula I:

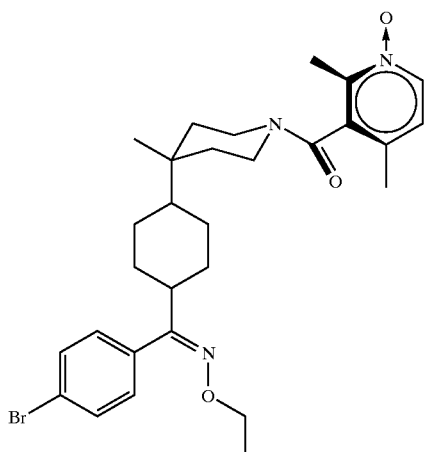

Structure A

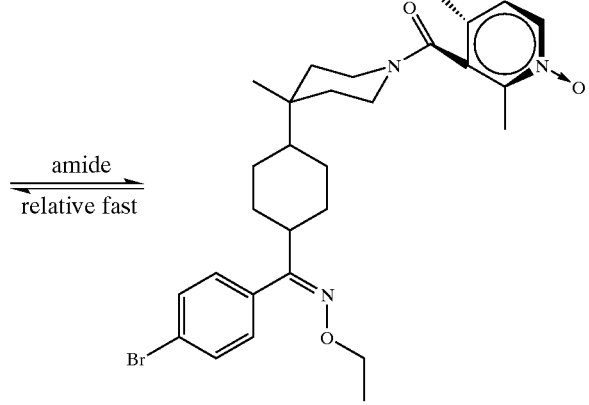

Structure 4

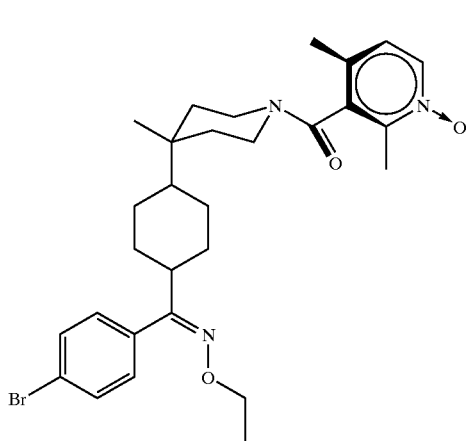

Structure 3

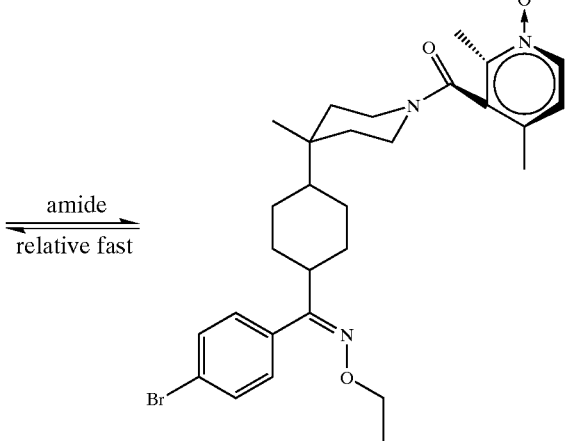

Structure B

37. A dibenzoyl-(L)-tartarate salt of a basic compound, wherein said basic compound has the formula:

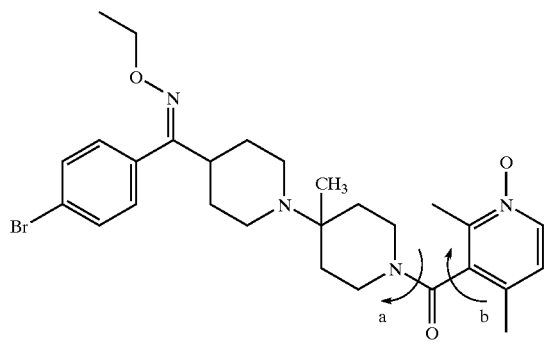

Formula I wherein said salt exists as a mixture of rotamers or rotamer pairs with said mixture comprising either (i) the 1-rotamer of said salt in a higher molar percent than the 2-rotamer, or (ii) the 2-rotamer of said salt in a higher molar percent than the 1-isomer, or (iii) the 1,2-rotamer pair of said salt in a higher molar percent than the 3,4-rotamer pair, or (iv) the 3,4-rotamer pair of said salt in a higher molar percent than the 1,2-rotamer pair, further wherein said 1-rotamer (structure A), 2-rotamer (structure B), 3-rotamer (structure C) and 4-rotamer (structure D) elute in the order 1, 2, 3 and 4 from a chiral HPLC column, and are shown by their following diastereomeric structures due to restricted rotation of bonds marked a and b in Formula I:

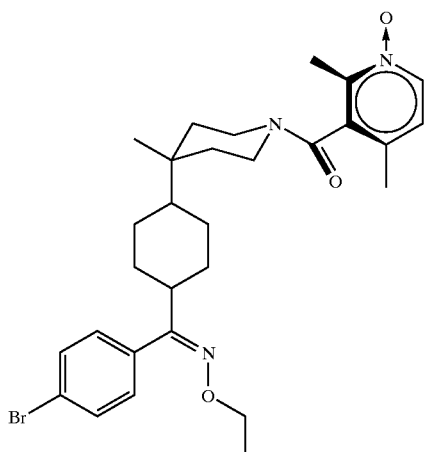

Structure A

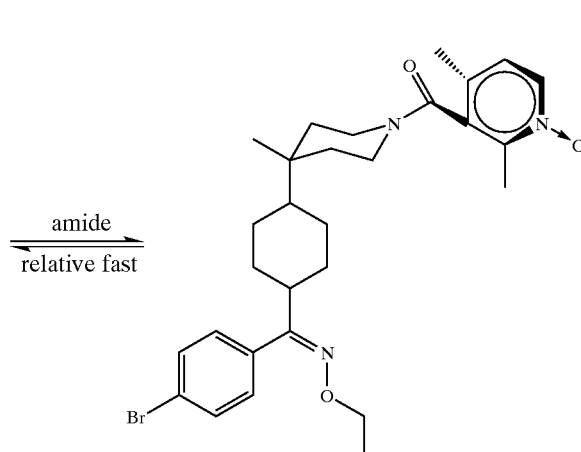

Structure 4

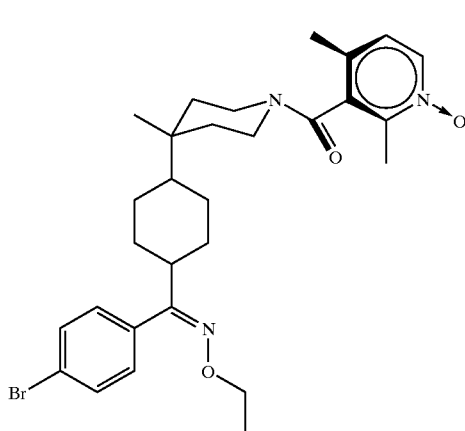

Structure 3

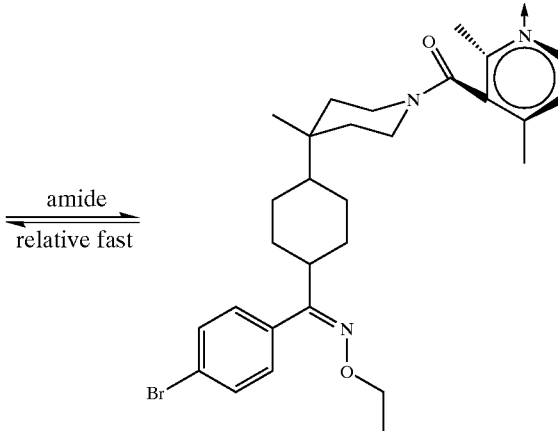

Structure B

38. A malate salt of a basic compound, wherein said basic compound has the formula:

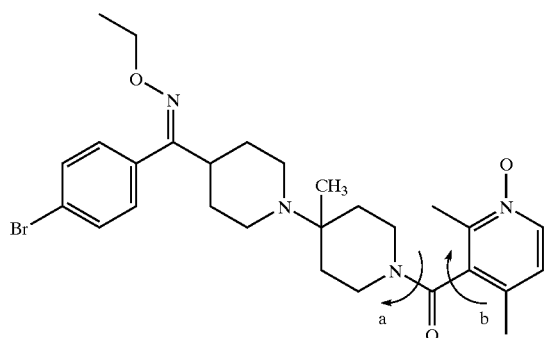

Formula I wherein said salt exists as a mixture of rotamers or rotamer pairs with said mixture comprising either (i) the 1-rotamer of said salt in a higher molar percent than the 2-rotamer, or (ii) the 2-rotamer of said salt in a higher molar percent than the 1-isomer, or (iii) the 1,2-rotamer pair of said salt in a higher molar percent than the 3,4-rotamer pair, or (iv) the 3,4-rotamer pair of said salt in a higher molar percent than the 1,2-rotamer pair, further wherein said 1-rotamer (structure A), 2-rotamer (structure B), 3-rotamer (structure C) and 4-rotamer (structure D) elute in the order 1, 2, 3 and 4 from a chiral HPLC column, and are shown by their following diastereomeric structures due to restricted rotation of bonds marked a and b in Formula I:

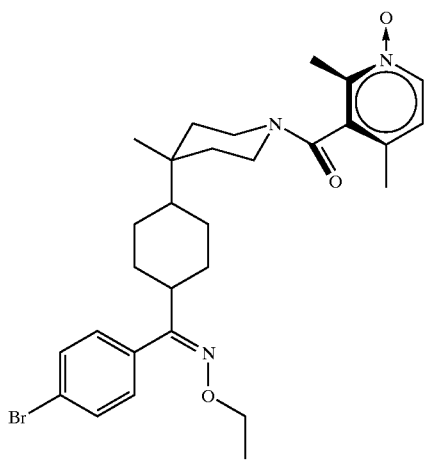

Structure A

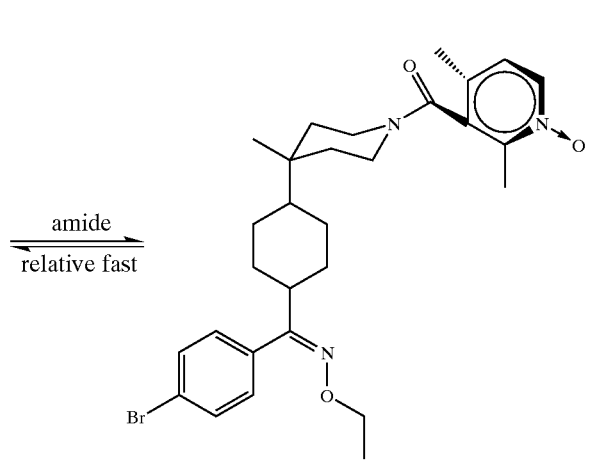

Structure 4 amide
relative fast aromatic
relative
slow aromatic
relative
slow

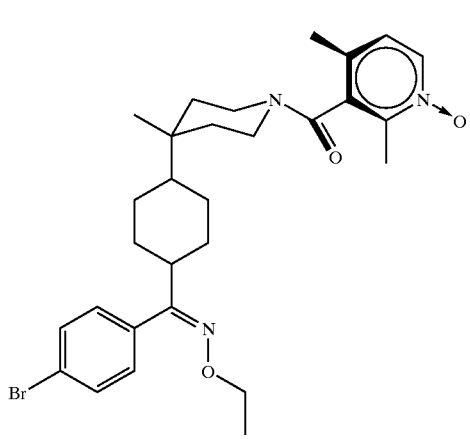

Structure 3

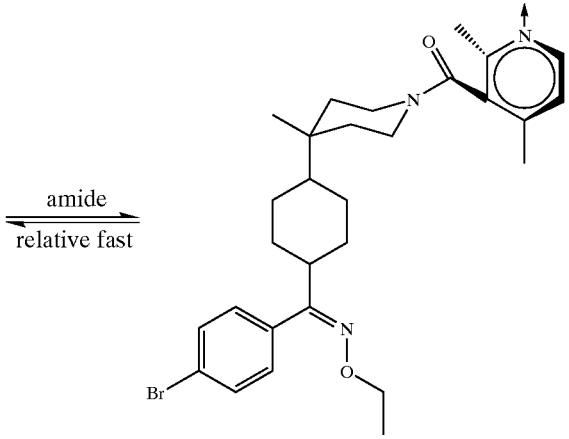

Structure B amide
relative fast

39. A p-toluenesulfonate salt of a basic compound, wherein said basic compound has the formula:

Formula I

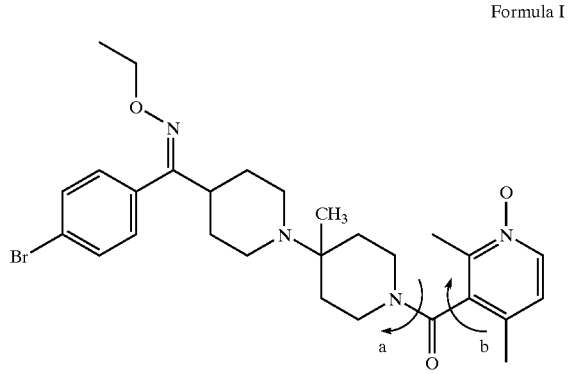

wherein said salt exists as a mixture of rotamers or rotamer pairs with said mixture comprising either (i) the 1-rotamer of said salt in a higher molar percent than the 2-rotamer, or (ii) the 2-rotamer of said salt in a higher molar percent than the 1-isomer, or (iii) the 1,2-rotamer pair of said salt in a higher molar percent than the 3,4-rotamer pair, or (iv) the 3,4-rotamer pair of said salt in a higher molar percent than the 1,2-rotamer pair, further wherein said 1-rotamer (structure A), 2-rotamer (structure B), 3-rotamer (structure C) and 4-rotamer (structure D) elute in the order 1, 2, 3 and 4 from a chiral HPLC column, and are shown by their following diastereomeric structures due to restricted rotation of bonds marked a and b in Formula I:

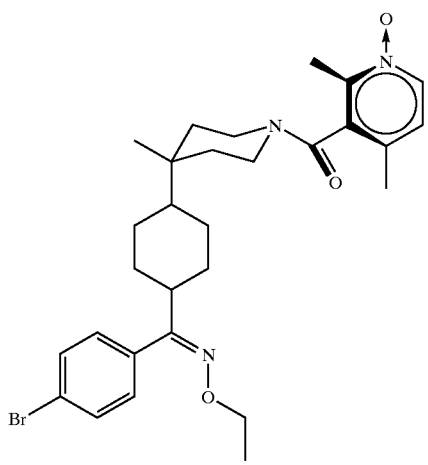

Structure A

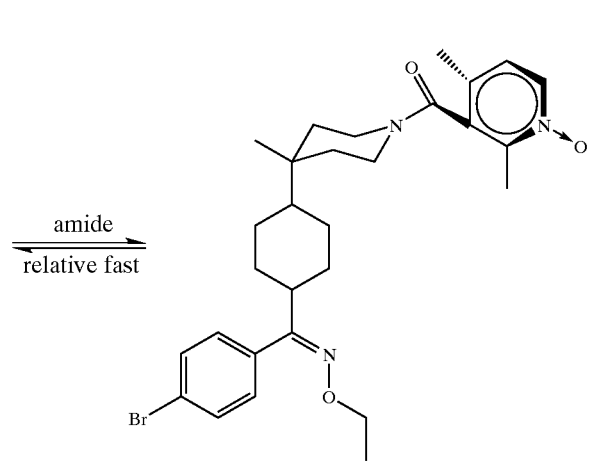

Structure 4

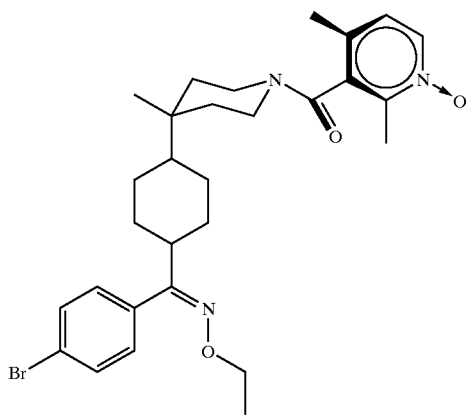

Structure 3

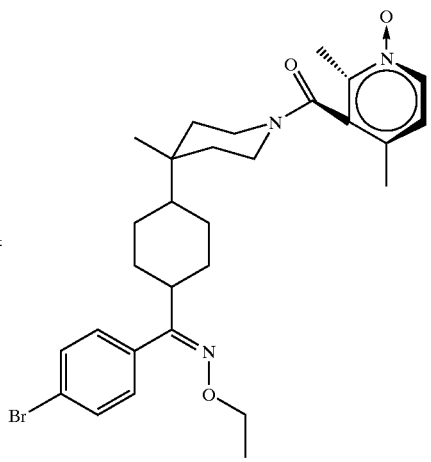

Structure B

* * * * *

UNITED STATES PATENT AND TRADEMARK OFFICE
CERTIFICATE OF CORRECTION

PATENT NO. : 6,936,718 B2  
APPLICATION NO. : 10/305100  
DATED : August 30, 2005  
INVENTOR(S) : Minzhang Chen Page 1 of 2

It is certified that error appears in the above-identified patent and that said Letters Patent is hereby corrected as shown below:

Replace the Figure appearing in each of claims 1, 23, and 30 to 39 with the following Figure:

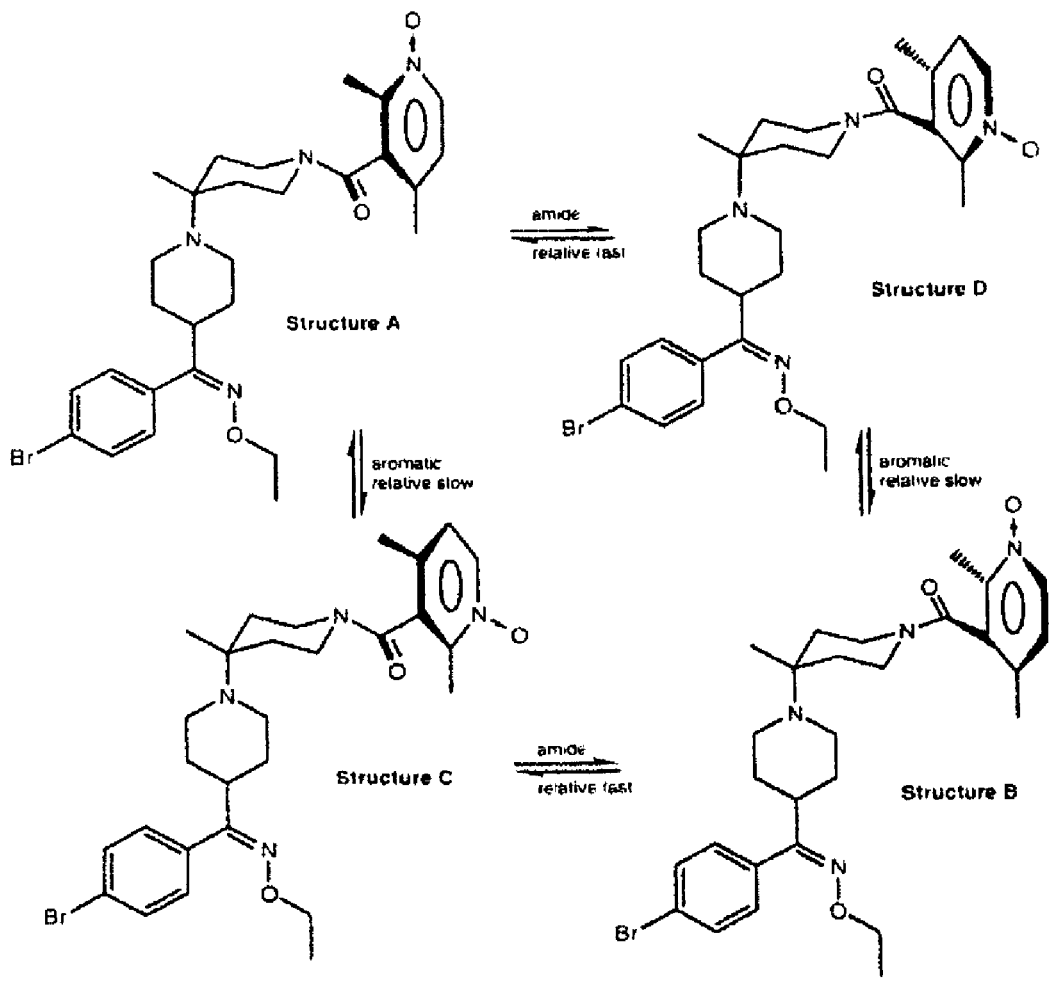

UNITED STATES PATENT AND TRADEMARK OFFICE
CERTIFICATE OF CORRECTION

PATENT NO. : 6,936,718 B2
APPLICATION NO. : 10/305100
DATED : August 30, 2005
INVENTOR(S) : Minzhang Chen It is certified that error appears in the above-identified patent and that said Letters Patent is hereby corrected as shown below:

Col. 19, line 8, claim 17, should read: The process of claim 15, wherein said dibenzoyl tartaric acid is the (L) acid.

Claim 30, Col. 22, line 56, delete "sah" insert in its place --salt--.

Signed and Sealed this

Sixteenth Day of December, 2008

JON W. DUDAS
*Director of the United States Patent and Trademark Office*